US012672977B2

(12) United States Patent
Herold et al.

(10) Patent No.: US 12,672,977 B2
(45) Date of Patent: Jul. 7, 2026

(54) MONITOR DEVICE WITH HUMAN-READABLE IDENTIFIER

(71) Applicant: Coloplast A/S, Humlebaek (DK)

(72) Inventors: Jakob Zeilberger Herold, Herlev (DK); Hans Jacob Henriksen, Vallensbaek (DK); Stephanie Knoedler, Nivaa (DK); Jais Ask Hansen, Jaegerspris (DK)

(73) Assignee: Coloplast A/S, Humlebaek (DK)

( * ) Notice: Subject to any disclaimer, the term of this patent is extended or adjusted under 35 U.S.C. 154(b) by 704 days.

(21) Appl. No.: 17/912,891

(22) PCT Filed: Mar. 22, 2021

(86) PCT No.: PCT/DK2021/050087
§ 371 (c)(1),
(2) Date: Sep. 20, 2022

(87) PCT Pub. No.: WO2021/185425
PCT Pub. Date: Sep. 23, 2021

(65) Prior Publication Data
US 2024/0009019 A1      Jan. 11, 2024

(30) Foreign Application Priority Data
Mar. 20, 2020      (DK) ........................... PA 2020 70173

(51) Int. Cl.
*A61F 5/445*          (2006.01)
*A61F 5/44*            (2006.01)
(52) U.S. Cl.
CPC ............ *A61F 5/4404* (2013.01); *A61F 5/445* (2013.01)

(58) Field of Classification Search
CPC ............................... A61F 5/4404; A61F 5/445
See application file for complete search history.

(56) References Cited

U.S. PATENT DOCUMENTS

| | | | | |
|---|---|---|---|---|
| 11,534,323 B2 * | 12/2022 | Hansen | ................... | G16H 30/40 |
| 2009/0322513 A1 * | 12/2009 | Hwang | ................... | H04W 4/90 |
| | | | | 600/301 |
| 2019/0117067 A1 * | 4/2019 | Konno | ................ | A61B 5/0002 |
| 2019/0133812 A1 * | 5/2019 | Seres | ..................... | A61F 5/443 |
| 2020/0375784 A1 * | 12/2020 | Hansen | .................. | A61F 5/443 |

(Continued)

FOREIGN PATENT DOCUMENTS

| | | |
|---|---|---|
| DE | 102008036820 A1 | 2/2010 |
| WO | 2005043350 A2 | 5/2005 |

(Continued)

*Primary Examiner* — Guy K Townsend
(74) *Attorney, Agent, or Firm* — Coloplast Corp., Coloplast A/S; Nick Baumann

(57) ABSTRACT

Embodiments disclosed herein relate to one or more monitoring devices with human-readable identifiers. In an exemplary embodiment, an ostomy system comprises an ostomy appliance comprising a sensor assembly and at least two monitor devices. The at least two monitor devices comprise a first monitor device and a second monitor device. Each of the at least two monitor 5 devices is configured to collect data from the sensor assembly. Further, the first monitor device comprises a first human-readable identifier and the second monitor device comprises a second human-readable identifier that is different from the first human-readable identifier.

15 Claims, 14 Drawing Sheets

(56)                    References Cited

U.S. PATENT DOCUMENTS

| | | | | |
|---|---|---|---|---|
| 2020/0375785 A1* | 12/2020 | Hansen | ................ | A61B 90/361 |
| 2020/0390587 A1* | 12/2020 | Svanegaard | ........... | G16H 40/40 |
| 2020/0395120 A1* | 12/2020 | Svanegaard | .......... | A61F 5/4404 |
| 2020/0405230 A1* | 12/2020 | Svanegaard | ......... | A61B 5/6813 |
| 2021/0000414 A1* | 1/2021 | Svanegaard | .......... | A61F 5/4404 |
| 2021/0007663 A1* | 1/2021 | Svanegaard | ........... | G16H 40/40 |
| 2021/0007881 A1* | 1/2021 | Svanegaard | .......... | A61F 5/4404 |
| 2021/0059603 A1* | 3/2021 | Svanegaard | ......... | A61B 5/4851 |
| 2022/0117771 A1* | 4/2022 | Fearn | ..................... | A61F 5/445 |
| 2022/0378602 A1* | 12/2022 | Hansen | ................ | A61F 5/4404 |
| 2023/0030622 A1* | 2/2023 | Nielsen | .................. | A61F 5/443 |

FOREIGN PATENT DOCUMENTS

| | | | | | |
|---|---|---|---|---|---|
| WO | 2010015390 | A1 | 2/2010 | | |
| WO | 2014151925 | A1 | 9/2014 | | |
| WO | 2019174692 | A1 | 9/2019 | | |
| WO | WO-2019174699 | A1 * | 9/2019 | ........... | A61B 5/4851 |
| WO | 2020035121 | A1 | 2/2020 | | |

* cited by examiner

300

6A

26C

6B

26CC

400

MONITOR DEVICE WITH HUMAN-READABLE IDENTIFIER

The present disclosure relates to an ostomy system comprising at least two monitor devices, each of which having a human-readable identifier. Further, the present disclosure relates to an accessory device forming part of the ostomy system and being configured to communicate with the at least two monitor devices.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
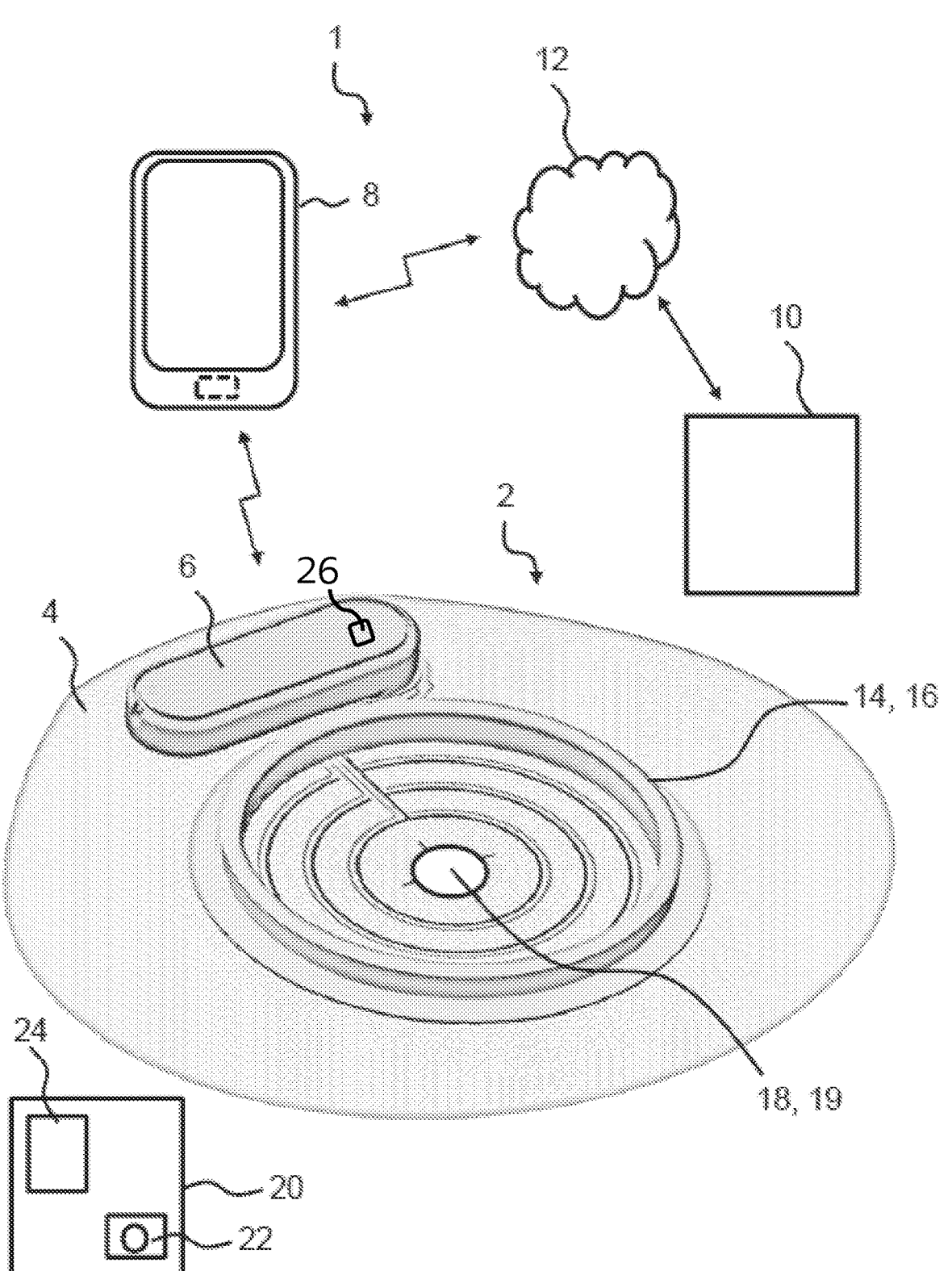
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," "liquids," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do not provide the effect.

The present disclosure relates to an ostomy system and devices thereof, such as an ostomy appliance, a base plate for an ostomy appliance, a sensor patch for application to a baseplate, one or more monitor devices, and optionally one or more accessory devices. Further, methods related to the ostomy system and devices thereof are disclosed. An accessory device (also referred to as an external device) can be a mobile phone or other handheld device. In embodiments, an accessory device is a personal electronic device, e.g. a wearable, such as a watch or other wrist-worn electronic device. An accessory device can be a docking station. In embodiments, the docking station is configured to electrically and/or mechanically couple the monitor device to the docking station. In embodiments, the docking station is configured for charging a battery of the monitor device and/or configured for transferring data between the monitor device and the docking station. The ostomy system can comprise a server device. In embodiments, the server device is operated and/or controlled by the ostomy appliance manufacturer and/or a service centre.

The present disclosure provides an ostomy system and devices thereof, such as an ostomy appliance, a base plate for an ostomy appliance, a sensor patch for application to a base plate, a monitor device, and optionally one or more accessory devices which either alone or together facilitate reliable determination of the nature, severity, and rapidness of moisture propagation in the adhesive material provided for attaching the base plate and/or sensor patch to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

In embodiments, the ostomy appliance comprises a base plate and an ostomy pouch (also referred to as an ostomy bag). The ostomy appliance can be a colostomy appliance, an ileostomy appliance, or a urostomy appliance. In embodiments, the ostomy appliance is a two-part ostomy appliance, i.e. the base plate and the ostomy pouch are releasably coupled e.g. with a mechanical and/or an adhesive coupling, e.g. to allow that a plurality of ostomy pouches can be utilized (exchanged) with one base plate. Further, a two-part ostomy appliance can facilitate correct application of the base plate to skin, e.g. to an improved user sight of the stomal region. In embodiments, the ostomy appliance is a one-part ostomy appliance, i.e. the base plate and the ostomy pouch are fixedly attached to each other. The base plate is configured for coupling to a user's stoma and/or skin surrounding the stoma, such as a peristomal skin area.

In embodiments, the ostomy appliance includes a base plate, such as a monolithic, one-piece base plate, e.g. integrated with a sensor assembly part, or a separate sensor assembly part, such as a sensor assembly part to be subsequently applied to a base plate. In embodiments, the sensor assembly part is a sensor patch for application to the base plate, such as the proximal surface of the base plate. Thereby, an arbitrary base plate, such as a conventional base plate, can achieve the features as described herein. Features as described with respect to sensing/monitoring capabilities of the base plate herein can be provided by a sensor assembly of a sensor patch to be applied to a base plate, e.g. by the user, and vice versa. In embodiments, the sensor patch is adapted to adhere to a base plate.

In embodiments, a method of attaching a base plate having sensing capabilities, e.g. through the provision of a sensor patch, to a user's stoma and/or skin surrounding the stoma, such as the peristomal skin area, comprises attaching the sensor patch to a base plate and attaching the base plate, i.e. together with the attached sensor patch, to the user's stoma and/or skin surrounding the stoma, such as the peristomal skin area. Alternatively, the method of attaching the base plate to the user's stoma and/or skin surrounding the stoma comprises attaching the sensor patch to the user's stoma and/or skin surrounding the stoma and attaching the base plate to the user's stoma and/or skin surrounding the stoma above the attached sensor patch, i.e. on a distal surface of the sensor patch.

In embodiments, the base plate and/or the sensor patch comprises a first adhesive layer with a proximal side configured for attachment of the base plate and/or the sensor patch to the skin surface of a user. In embodiments, the first adhesive layer has a stomal opening, such as a first adhesive stomal opening, with a centre point.

In embodiments, the base plate and/or sensor patch comprises a plurality of electrodes including a first leakage electrode, a second leakage electrode, and a third leakage electrode provided in an electrode assembly of a sensor assembly. In embodiments, the plurality of electrodes is configured to detect presence of liquid, such as output, on the proximal side of the first adhesive layer and/or moisture content in the first adhesive layer. In embodiments, the electrode assembly of the sensor assembly is configured to detect presence of liquid, such as output, on the proximal side of the first adhesive layer and/or moisture content in the first adhesive layer in a primary sensing zone and a secondary sensing zone. In embodiments, the primary sensing zone is arranged in a primary angle space from the centre point of the first adhesive layer, and/or the secondary sensing zone is arranged in a secondary angle space from the centre point of the first adhesive layer. Alternatively, or additionally, the primary sensing zone can be arranged in a primary radial space from the centre point of the first adhesive layer and the secondary sensing zone can be arranged in a secondary radial space from the centre point of the first adhesive layer. In embodiments, the electrode assembly of the sensor assembly is configured to detect presence of liquid, such as output, on the proximal side of the first adhesive layer and/or moisture content in the first adhesive layer in three or more sensing zones.

In embodiments, the monitor device comprises a housing, a rechargeable battery, a processor, a memory, a first interface (also referred to as an appliance interface) connected to the processor and the memory, and a second interface connected to the processor. The first interface is configured for obtaining ostomy data from the base plate and/or the sensor patch coupled to the first interface. The ostomy data comprises primary ostomy data from a primary electrode set of the base plate and/or the sensor patch, and secondary ostomy data from a secondary electrode set of the base plate and/or the sensor patch. In embodiments, the processor is configured to: obtain primary parameter data based on the primary ostomy data; obtain secondary parameter data based on the secondary ostomy data; and detect presence of liquid on the proximal side of the first adhesive layer and/or moisture in the first adhesive layer in a primary sensing zone based on the primary parameter data. In embodiments, the primary sensing zone is arranged in a primary angle space from the centre point of the first adhesive layer and/or arranged in a primary radial space from the centre point of the first adhesive layer. Further, in embodiments, the processor is configured to detect presence of liquid on the proximal side of the first adhesive layer and/or moisture in the first adhesive layer in a secondary sensing zone based on the secondary parameter data. In embodiments, the secondary sensing zone is arranged in a secondary angle space from the centre point of the first adhesive layer and/or arranged in a secondary radial space from the centre point of the first adhesive layer. In embodiments, in accordance with a detection of presence of liquid and/or moisture in the primary sensing zone, the processor is configured to transmit a primary monitor signal comprising monitor data indicative of presence of liquid and/or moisture in the primary sensing zone via the second interface; and in accordance with a detection of presence of liquid and/or moisture in the secondary sensing zone, transmit a secondary monitor signal comprising monitor data indicative of presence of liquid and/or moisture in the secondary sensing zone via the second interface.

According to certain embodiments, the user is provided with at least two monitor devices for practical reasons. This allows, for instance, one device to be in use and the other device to be recharged. The devices are interchangeable and can perform the same functions. The devices also look identical, but the user must be able to reliable distinguish between the two devices, for instance if one has a low battery level and the other is fully charged. The present invention solves this by providing on each monitor device a unique human-readable identifier, for instance in the form of a symbol or a combination of characters. This facilitates the human-machine interaction by making it easy for the user to input to the accessory device which devices are available, and by allowing the system to easily identify to the user the operating status of each device. For instance, the user will inform the accessory device that the two devices available to the user have different, respective human-readable identifiers. The system will then, whenever providing information to the user about the devices, identify them by their human-readable identifiers, for instance letting the user know to change device from monitor device A to monitor device B because the former is running out of battery and needs recharging.

The base plate and/or the sensor patch comprises a first adhesive layer. During use, the first adhesive layer adheres to the user's skin (peristomal area) and/or to additional seals, such as sealing paste, sealing tape and/or sealing ring. Thus, in embodiments, the first adhesive layer is configured for attachment of the base plate and/or the sensor patch to the skin surface of a user. In embodiments, the first adhesive layer has a stomal opening, such as a first adhesive stomal opening, with a centre point or is at least prepared for forming a stomal opening with a centre point. A base plate and/or a sensor patch according to the present disclosure enables detection of presence of liquid or output on the proximal side of the first adhesive layer (between a skin surface of the user, such as the peristomal skin area, and the proximal surface of the first adhesive layer).

In embodiments, the first adhesive layer is made of a first composition. In embodiments, the first composition comprises one or more polyisobutenes and/or styrene-isoprene-styrene. In embodiments, the first composition comprises one or more hydrocolloids. In embodiments, the first composition comprises one or more water soluble or water swellable hydrocolloids. In embodiments, the first composition is a pressure sensitive adhesive composition suitable for medical purposes comprising a rubbery elastomeric base and one or more water soluble or water swellable hydrocolloids. In embodiments, the first composition comprises one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. For example, the styrene copolymer can be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semi-synthetic hydrocolloids, and synthetic hydrocolloids. The first composition can comprise 20-60% hydrocolloids. A preferred hydrocolloid is carboxymethyl cellulose (CMC). Optionally, the first composition can contain other components, such as fillers, tackifiers, plasticizers, and/or other additives.

The first adhesive layer can have a substantially uniform thickness. The first adhesive layer can have a thickness in the range from 0.1 mm to 1.5 mm, e.g. in the range from 0.2 mm to 1.2 mm, such as 0.8 mm or 1.0 mm. The first adhesive layer can have a primary thickness in a primary part of the first adhesive layer, e.g. in a primary region within a primary radial distance or in a primary radial distance range from the centre point of the stomal opening. The primary thickness can be in the range from 0.2 mm to 1.5 mm. such as about 1.0 mm. The primary radial distance can be in the range from 20 mm to 50 mm, such as in the range from 25 mm to 35 mm, e.g. 30 mm. The first adhesive layer can have a secondary thickness in a secondary part of the first adhesive layer, e.g. in a secondary region outside a secondary radial distance or in a secondary radial distance range from the centre point of the stomal opening. The secondary thickness can be in the range from 0.2 mm to 1.0 mm, such as about 0.5 mm. The secondary radial distance can be in the range from 20 mm to 50 mm, such as in the range from 25 mm to 35 mm, e.g. 30 mm.

In embodiments, the base plate and/or the sensor patch comprises a second layer. In embodiments, the second layer is an adhesive layer. In embodiments, the second layer has a second radial extension that is larger than a first radial extension of the first adhesive layer at least in a first angular range of the base plate and/or the sensor patch. Accordingly, a part of a proximal surface of the second layer can be configured for attachment to the skin surface of a user. The part of a proximal surface of the second layer configured for attachment to the skin surface of a user is also denoted the skin attachment surface of the second adhesive layer. The second layer can have a stomal opening, such as a second layer stomal opening and/or a second adhesive stomal opening, with a centre point.

In embodiments, the second adhesive layer is made of a second composition. In embodiments, the second composition comprises one or more polyisobutenes and/or styrene-isoprene-styrene. In embodiments, the second composition comprises one or more hydrocolloids. In embodiments, the second composition comprises one or more water soluble or water swellable hydrocolloids. In embodiments, the second composition is a pressure sensitive adhesive composition suitable for medical purposes comprising a rubbery elastomeric base and one or more water soluble or water swellable hydrocolloids. In embodiments, the second composition comprises one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. For example, the styrene copolymer can be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition can comprise 20-60% hydrocolloids. A preferred hydrocolloid is carboxymethyl cellulose (CMC). Optionally, the second composition can contain other components, such as fillers, tackifiers, plasticizers, and/or other additives.

Different ratio of contents can change properties of the first and/or second adhesive layers. In embodiments, the second adhesive layer and the first adhesive layer have different properties. In embodiments, the second adhesive layer (second composition) and the first adhesive layer (first composition) have different ratios of polyisobutenes, styrene-isoprene-styrene, and/or hydrocolloids. For example, the second adhesive layer can provide a stronger attachment to the skin compared to attachment to the skin provided by the first adhesive layer. Alternatively, or additionally, the second adhesive layer can be thinner than the first adhesive layer. Alternatively, or additionally, the second adhesive layer can be less water and/or sweat absorbing than the first adhesive layer. Alternatively, or additionally, the second adhesive layer can be less moldable than the first adhesive layer. In embodiments, the second adhesive layer provides a second barrier against leakage.

The second layer can have a substantially uniform thickness. The second layer can have a thickness in the range from 0.1 mm to 1.5 mm, e.g. in the range from 0.2 mm to 1.0 mm, such as 0.5 mm, 0.6 mm, or 0.7 mm.

Providing a base plate having sensing capabilities, e.g. through an incorporated sensor assembly or through a sensor patch comprising a sensor assembly, provides for an optimum or improved use of an ostomy appliance. In particular, it is facilitated that a base plate is not changed too late (leading to adhesive failure, leakage and/or skin damage), or at least that a user is informed that a leakage will happen, is happening, or has happened. Accordingly, the user or a health care professional is able to monitor and plan the use of the ostomy appliance.

In embodiments, the base plate and/or the sensor patch comprises one or more electrodes, such as a plurality of electrodes, such as two, three, four, five, six, seven or more electrodes. The sensor patch can be applied to the base plate, such as to provide the base plate with the one or more electrodes. In embodiments, the electrodes are provided in an electrode assembly. In embodiments, the electrode assembly is provided in a sensor assembly.

In embodiments, the electrodes, e.g. some or all the electrodes, are arranged between the first adhesive layer and the second adhesive layer. In embodiments, the electrodes are arranged in an electrode assembly, e.g. an electrode layer of a sensor assembly. In embodiments, an electrode comprises a connection part for connecting the electrodes to other components and/or interface terminals/terminal elements, such as for connecting the electrodes to a monitor device. In embodiments, an electrode comprises one or more conductor parts and/or one or more sensing parts. A conductor part can be considered part of an electrode connecting two or more sensing parts, and/or connecting a sensing part with a connection part of the respective electrode. A sensing part can be considered a part of the electrode being suitable for sensing, e.g. liquid, such as liquid content, and/or output, such as output resulting from a leakage, or an imminent leakage. The sensing part can be suitable for sensing e.g. by its shape, said shape potentially being circular, oval, or rectangular. Thus, the conductor part can conduct a signal arising from the sensing part. In embodiments, an electrode comprises alternating conductor parts and sensing parts. In embodiments, the electrode assembly is arranged between the first adhesive layer and the second adhesive layer. The base plate and/or the sensor patch, e.g. the electrode assembly, can comprise a first electrode, a second electrode and optionally a third electrode. The base plate and/or the sensor patch, e.g. the electrode assembly, can comprise a fourth electrode and/or a fifth electrode. The base plate and/or the sensor patch, e.g. the electrode assembly, optionally comprises a sixth electrode. In embodiments, the base plate and/or the sensor patch, e.g. the electrode assembly, comprises a ground electrode. The ground electrode can comprise a first electrode part. In embodiments, the first electrode part of the ground electrode forms a ground or reference for the first electrode. In embodiments, the first electrode part forms a closed loop. The ground electrode can comprise a second electrode part. In embodiments, the second electrode part of the ground electrode forms a ground or reference for the second electrode. The ground electrode can comprise a third electrode part. In embodiments, the third electrode part of the ground electrode forms a ground or reference for the third electrode. The ground electrode can comprise a fourth electrode part. In embodiments, the fourth electrode part of the ground electrode forms a ground or reference for the fourth electrode and/or the fifth electrode. In embodiments, the ground electrode is configured as or forms a (common) reference electrode for some or all of the other electrodes of the electrode assembly.

The electrodes are electrically conductive and can comprise one or more of metallic (e.g. silver, copper, gold, titanium, aluminium, stainless steel), ceramic (e.g. ITO), polymeric (e.g. PEDOT, PAN I, PPy), and carbonaceous (e.g. carbon black, carbon nanotube, carbon fibre, graphene, graphite) materials.

In embodiments, the electrode assembly comprises a support layer, also denoted a support film. In embodiments, the sensor assembly comprises the electrode assembly and the support layer. One or more electrodes can be formed, e.g. printed, on the proximal side of the support layer. One or more electrodes can be formed, e.g. printed, on the distal side of the support layer. Thus, one or more electrodes can be arranged between the support layer and the first adhesive layer. The electrode assembly, such as the support layer of the electrode assembly, can have a stomal opening, such as an electrode assembly stomal opening and/or a support layer stomal opening, with a centre point. In embodiments, the support layer comprises polymeric (e.g. polyurethane, PTFE, PVDF) and/or ceramic (e.g. alumina, silica) materials. In one or more exemplary base plates and/or sensor patches, the support layer is made of thermoplastic polyurethane (TPU). The support layer material can be made of or comprise one or more of polyester, a thermoplastic elastomer (TPE), polyimide, polyimide, ethylene-vinyl acetate (EVA), polyurea, and silicones. Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

Determination of moisture pattern types or angular leakage patterns is useful in helping to reduce the risk of a user experiencing leakage from an ostomy appliance. Further, determination of moisture pattern types and classification of operating states and/or leakage patterns of the ostomy appliance is further useful in helping reduce the risk of skin damage to a user.

In embodiments, two electrodes of the electrode assembly form a sensor. In embodiments, the first leakage electrode and the second leakage electrode form a primary leakage sensor or primary leakage electrode pair for detecting presence of liquid on the proximal side of the first adhesive layer in the primary sensing zone. In embodiments, the second leakage electrode and the third leakage electrode form a secondary leakage sensor or secondary leakage electrode pair for detecting presence of liquid on the proximal side of the first adhesive layer in the secondary sensing zone. In embodiments, the first leakage electrode and the third leakage electrode form a tertiary leakage sensor or tertiary leakage electrode pair for detecting presence of liquid on the proximal side of the first adhesive layer in the tertiary sensing zone.

In embodiments, the base plate and/or the sensor patch comprises a monitor interface (also referred to as an assembly interface). In embodiments, the monitor interface is configured for electrically and/or mechanically connecting the ostomy appliance (base plate and/or sensor patch) to the monitor device. In embodiments, the monitor interface is configured for wirelessly connecting the ostomy appliance (base plate and/or sensor patch) to the monitor device. Thus, the monitor interface of the base plate and/or the sensor patch can be configured to electrically and/or mechanically couple the ostomy appliance and the monitor device.

In embodiments, the monitor interface of the base plate and/or the sensor patch comprises, e.g. as part of a first connector of the monitor interface, a coupling part for forming a mechanical connection, such as a releasable coupling between the monitor device and the base plate and/or the sensor patch. In embodiments, the coupling part is configured to engage with a coupling part of the monitor device for releasably coupling the monitor device to the base plate and/or the sensor patch.

According to certain embodiments, the present disclosure provides an ostomy system comprising two monitor devices including human-readable identifiers, a kit of parts having monitor devices including human-readable identifiers, a monitor device including a human-readable identifier, and a method of providing at least two monitor devices including human-readable identifiers.

In a first aspect of the invention, an ostomy system is disclosed. The ostomy system comprises an ostomy appliance and at least two monitor devices. The ostomy appliance comprises a sensor assembly. The at least two monitor devices includes a first monitor device and a second monitor device. Each of the at least two monitor devices are configured to collect data from the sensor assembly. The first monitor device comprises a first human-readable identifier and the second monitor device comprises a second human-readable identifier being different from the first human-readable identifier. In other words, the first human-readable identifier of the first monitor device is different from the second human-readable identifier of the second monitor device, thereby providing means for distinguishing the two monitor devices.

Each of the at least two monitor devices comprises means for collecting data from the sensor assembly. For example, in embodiments, each of the at least two monitor devices comprises a housing, a power source, such as a rechargeable battery, a processor, and an interface configured to wirelessly and/or mechanically connect to a sensor of the sensor assembly, such as an electrode of the sensor assembly.

As stated above, according to certain embodiments, the user is provided with at least two monitor devices. For example, a user is provided with an ostomy system according to the first aspect of the invention. This allows, for instance, one monitor device to be in use and the other monitor device to be recharged. The monitor devices are interchangeable and can perform the same functions. The monitor devices may also look identical, but the user must be able to reliably distinguish between the two monitor devices, for instance if one has a low battery level and the other is fully charged.

The present invention solves this by providing on each monitor device a unique human-readable identifier, for instance in the form of a symbol or a combination of characters. This facilitates the human-machine interaction by making it easy for the user to input to an accessory device, e.g. a smart device (e.g. a smartphone) or a computer, which monitor devices are available, and by allowing the system to easily identify to the user the operating status of each monitor device. For instance, the user will inform the accessory device that the two monitor devices available to the user have different, respective human readable identifiers. The system will then, whenever providing information to the user about the monitor devices, identify them by their human readable identifiers, for instance letting the user know to change the monitor device from monitor device A to monitor device B because the former is running out of battery and needs recharging. In embodiments, the human-readable identifiers of a given ostomy system are provided in the same format or representation. For example, the format may be a certain length of a character string, a certain matrix format (e.g., 2×2) or belong to a certain group of symbols.

The present invention solves the technical problem of how to make it easy for a user to select and put into use a specific monitor device from a number of similar or identical monitor devices based on input from an accessory device of the ostomy system. The technical effect is that each individual monitor device can reliably be handled and used appropriately by the user based on the internal state and/or operating status of all available monitor devices as identified by the accessory device.

For instance, the accessory device has information about the battery level of all monitor devices and is able to unambiguously let the user know which monitor device to use and which monitor device to recharge. The human-readable identifier provides the technical link between the user and the accessory device, which allows the user to operate and use the monitor device in the appropriate technical manner.

By a human-readable identifier is meant a representation of data or information that can be naturally read/interpreted by humans, such as, but not limited to, shorter names or strings, that are easier to comprehend or to remember than long, complex syntax notations. Thus, by human-readable is understood that the human brain is capable of quickly comprehending the data. Thereby, the human reading the human-readable identifier is capable of storing the identifier in his/her short-term memory with the purpose of inputting said identifier in an interface or identifying said identifier from a plurality, such as at least two, identifiers. Thus, a human-readable identifier is a representation of data (identifier) that is represented in an appropriate format and level of abstraction for human comprehension. According to research on short-term memory (Baddely: "Working Memory: Theories, Models, and Controversies", Annu. Rev. Psychol. 2012. 63: 1-29), the average human has the ability to review and store a string of up to seven characters in their short-term memory and recall the 7 characters for selection and/or input into an accessory device of the ostomy system. Therefore, in some instances, a human-readable identifier is a representation of a list/string of 7 or fewer characters. Humans are also able to recognize patterns and, therefore, in some instances, the human-readable identifiers include colours and/or colour schemes, design icons, geometric shapes, matrices having a limited number of characters (e.g., 4-letter matrices), and/or pie chart icons.

Examples of non-human-readable identifiers include barcodes, QR-codes, and longer character strings, such as strings including more than seven characters.

As an example, two monitor devices are used in an ostomy system: The first monitor device comprises the first human-readable identifier "AB12" and the second monitor device comprises the second human-readable identifier "CD34". Thereby, a user handling the first and second monitor devices is capable of distinguishing the two monitor devices, namely by the first monitor device having the identifier AB12 and the second monitor device having the identifier CD34.

The ostomy system according to the first aspect of the invention provides for using at least two monitor devices interchangeably, such that data collection is not interrupted by charging of one of the at least two monitor devices. Further, the ostomy system provides for an increased peace of mind, as the user can choose between two monitor devices, whereby malfunctioning or lack of power/battery does not obstruct data collection. Further, the ostomy system allows for the user to easily distinguish the two monitor devices, namely by each of the monitor devices having/carrying a mutually unique human-readable identifier.

In an embodiment, the ostomy system further comprises an accessory device. The accessory device comprises a first interface configured to communicate with each of the at least two monitor devices and a user interface configured to receive a user input indicative of the first and/or second human-readable identifier.

In embodiments, the user interface is a graphical user interface. In embodiments, the accessory device is a smart device, such as a smartphone or smartwatch comprising a touchscreen, such that the user input can be a touch input, and a processor. In embodiments, the accessory device is a computer. In embodiments, the first interface comprises a transceiver configured to communicate wirelessly with a transceiver of each of the at least two monitor devices, e.g. according to a Bluetooth protocol.

Thereby is provided an ostomy system capable of exchanging data between each of the at least two monitor devices and an accessory device, and a system where the processing power of the accessory device can be utilized.

In an embodiment, the accessory device, in accordance with receiving a first user input indicative of the first human-readable identifier, is configured to create a first monitor device profile and, in accordance with receiving a second user input indicative of the second human-readable identifier, is configured to create a second monitor device profile.

Thus, the accessory device is configured to receive a first user input being indicative of the first human-readable identifier and to receive a second user input being indicative of the second human-readable identifier. For example, the user interface of the accessory device is configured to allow the user to input the human-readable identifier, e.g. by inputting a string of characters corresponding to the human-readable identifier (in the situation of the human-readable identifier being a string or combination of characters). This example illustrates how the human-readable identifier is designed: to allow the user to easily read and comprehend the identifier, such that he/she can easily store the identifier in his/her short-term memory with the purpose of easily inputting the identifier in the user interface of the accessory device.

In embodiments, the first monitor device profile and the second monitor device profiles control how the accessory device communicates with the first and second monitor device. In embodiments, each of the first and second monitor devices profiles is visualized by a corresponding interactive graphical object on the (graphical) user interface. In embodiments, the interactive graphical object displays information, such as an operating status, pertaining to the corresponding monitor device.

The creation of a monitor device profile for each of the at least two monitor devices allows for the accessory device to distinguish the at least two monitor devices and to store information pertaining to each of the at least two monitor devices in separate data sets. Further, the visualization of each of the at least two monitor devices through a graphical object in the (graphical) user interface allows for the user to easily identify an operating status of each of the at least two monitor devices.

In exemplary embodiments, the ostomy system is used to monitor a plurality of users by means of a single accessory device. In such exemplary embodiments, the plurality of monitor devices is capable of collecting ostomy data from a plurality of ostomy appliances simultaneously and transmitting monitor data to the accessory device simultaneously. Thereby, from the first interface of the accessory device, a user, such as a health care professional, can monitor a plurality of users simultaneously. By means of the human-readable identifiers of the monitor devices in the ostomy system being different and by creating corresponding monitor device profiles in the accessory device, the user of the accessory device, such as the health care professional, can identify the specific user experiencing an issue with his/her ostomy appliance, such as leakage from the ostomy appliance, and thereby institute appropriate actions. Thus, in such exemplary embodiments, the different monitor device profiles correspond to different users.

In an embodiment, each of the first and second monitor device profiles is selectable by a user through the user interface, and the accessory device, in accordance with receiving a user input indicative of the first monitor device profile being selected, is configured to transmit a first device signal to the first monitor device indicative of the first monitor device profile being selected; and, in accordance with receiving a user input indicative of the second monitor device profile being selected, is configured to transmit a second device signal to the second monitor device indicative of the second monitor device profile being selected.

Thereby, the accessory device is configured to communicate with each of the at least two monitor devices separately and based on a selection made by the user. For example, the user can select (through a user input) the first monitor device profile, whereby a first device signal is transmitted to the first monitor device. Correspondingly, the user can select (through a user input) the second monitor device profile, whereby a second device signal is transmitted to the second monitor device. In embodiments, in accordance with selecting the first monitor device profile, a complimentary second device signal is transmitted to the second monitor device being indicative of the first monitor device profile being selected, and in accordance with selecting the second monitor device profile, a complimentary first device signal is transmitted to the first monitor device being indicative of the second monitor device profile being selected.

By the monitor device profiles being selectable, the user can send specific instructions (contained in the first and second device signals) to each of the at least two monitor devices. For example, the user can specify to the at least two monitor devices that he/she is selecting the first monitor device as the current data collecting device, e.g. by selecting the first monitor device profile. In embodiments, the selection of a specific monitor device profile (e.g., the first) instructs the corresponding specific (first) monitor device to start collecting data from the ostomy appliance.

In embodiments, the first/second monitor device profile is visualized in the (graphical) user interface of the accessory device together with the corresponding first/second human-readable identifier. Thereby, the user can easily identify which monitor device is related to which device profile.

In an embodiment, the user interface of the accessory device is configured to display an operating status of each of the at least two monitor devices. In an embodiment, the operating status is indicative of a battery level of a battery of each of the at least two monitor devices. In an embodiment, the operating status is indicative of a data collection mode of each of the at least two monitor devices.

In embodiments, the operating status is displayed in the graphical user interface, e.g. as part of a graphical object representing each of the first and second monitor device profiles. Thereby, for example, by reading the human-readable identifier displayed on/assigned to the given monitor device profile, the user can easily identify which monitor device of the at least two monitor devices has a low battery. For example, a user having the monitor devices with the identifiers AB12 and CD34 is capable of reading from the user interface of the accessory device that the monitor device AB12 is low on battery (e.g. due to use), whereas the monitor device CD34 is fully charged.

Thereby, the user can select the appropriate monitor device to use as the data collecting device, and e.g. to start charging of the other monitor device. In another example, the user can read that the monitor device AB12 is currently collecting data from the ostomy appliance and the monitor device CD34 is currently charging. Thus, the use of human-readable identifiers on the monitor devices provides for easily identifying which monitor device the accessory device is referring to.

In embodiments, the operating status is indicative of a data transmission mode, a connectivity mode, a wireless pairing mode, a data processing mode, or an on/off mode.

In an embodiment, the accessory device is configured to obtain first monitor data from the first monitor device and second monitor data from the second monitor device.

Thereby, the accessory device can process the monitor data. In embodiments, monitor data is based on ostomy data collected from the sensor assembly of the ostomy appliance. In embodiments, monitor data comprises ostomy data. In embodiments, monitor data comprises parameter data based on ostomy data. In embodiments, monitor data comprises sensor data, such as data from a sensor of the monitor device, such as an accelerometer, a temperature sensor, or a humidity sensor.

Thereby, a processing power of the accessory device can be utilized with the purpose of determining and/or communicating an operating state of the ostomy appliance. In embodiments, the operating state is indicative of the adhesive performance of the base plate of the ostomy appliance. In embodiments, the operating state is indicative of the presence of fluid, such as output, in an interface between the proximal surface of the base plate and a skin surface of the user. In embodiments, the operating state is indicative of an internal dynamic condition/state of the base plate.

In an embodiment, the accessory device is configured to pool the first monitor data and the second monitor data. By pooling data is meant to combine the data to form a single data set.

Thereby, the use of at least two monitor devices does not affect the overall purpose of monitoring the ostomy appliance. In other words, by pooling the data, the accessory device is capable of determining an operating state of the ostomy appliance even is the user changes the data collecting monitor device, as the data collected by the previous (e.g. first) monitor device is pooled with the data being collected by the active (e.g. second) monitor device. Thereby, a continuous/non-interrupted model of the ostomy appliance can be determined.

In an embodiment, each of the first and second human-readable identifiers comprises maximally four characters providing at least 50,000 different combinations. It is to be understood that, for each marking of a monitor device with a human-readable identifier, the maximally four characters are generated at random. Thereby, during manufacturing, a new human-readable identifier comprising maximally four characters providing at least 50,000 different combinations is generated at random for each monitor device in the production line.

In a preferred embodiment, each of the first and second human-readable identifiers comprises maximally four characters providing at least 50,000 different combinations, but in alternative embodiments, each of the first and second human-readable identifiers may comprise a string or matrix of characters providing at least 10,000 different combinations, or at least 25,000 different combinations, or at least 50,000 different combinations. In embodiments, the string or matrix of characters comprises between three and seven characters, such as three characters, four characters, five characters, six characters, or seven characters. By increasing the number of different combinations, the possibility of selecting, at random, two identical monitor devices (in terms of their identifiers) decreases, thus rendering the human-readable identifiers among two monitor devices increasingly effectively different. By reducing the number of characters in the string or matrix, such string or matrix becomes, for some users, increasingly easier to remember in the user's short-term memory, and thus increasingly human-readable within definitions provided herein.

In embodiments, the maximally four characters are provided in a string. In embodiments, the maximally four characters are provided in a matrix. In embodiments, the first and second human-readable identifiers are provided in the same format or representation. For example, the format may be a certain length of a character string (e.g., four characters) or a certain matrix format and size (e.g., a 2×2 matrix, thus comprising four characters).

The previous embodiments and examples illustrate the need for providing at least two monitor devices having different human-readable identifiers: if a user were to be provided two monitor devices having identical human-readable identifiers (or no identifiers at all), he/she would be unable to distinguish the monitor devices. However, the task of providing at least two monitor devices having different human-readable identifiers requires certain considerations to be made by the supplier/manufacturer. One such consideration includes how to make sure the ostomy system according to previous embodiments indeed comprises at least two monitor devices having different human-readable identifiers—and not identical human-readable identifiers.

By using a human-readable identifier providing for at least 50,000 different combinations, the supplier can select, at random, any two or more monitor devices from a plurality of monitor devices for a given ostomy system with a minimal risk of selecting two monitor devices having identical human-readable identifiers. In other words, when the human-readable identifier provides for at least 50,000 different combinations, and the human-readable identifier (e.g., a string of characters) is generated at random for each marking of a monitor device, the chances of selecting two monitor devices having identical human-readable identifiers are close to zero ($\frac{1}{50,000}$). Thereby, a reduced need to set up a system capable of selecting a second monitor device having a certain human-readable identifier different from a previously-selected first monitor device having a certain human-readable identifier is provided. In other words, when the number of different possible combinations of the human-readable identifiers is sufficiently high, e.g., 50,000, the supplier can select the second monitor device at random, without considering the identifier of the first monitor device. As such, due to the low possibility (e.g., <1:50,000) of selecting two monitor devices with identical human-readable identifiers, the first and second human-readable identifiers of the ostomy system may be considered effectively different.

At least 50,000 different combinations by means of maximally four characters can be created by combining letters from the English alphabet (26 letters) and Arabic numerals (10 numerals) (here, only considering a single case form selected from upper-case and lower-case letters). For example, the following combinations yield more than 50,000 different combinations: [letter][letter][letter][letter] yielding 26×26×26×26=456,976 different combinations, [letter][letter][letter][numeral] yielding 26×26×26×10=175,760 different combinations, and [letter][letter][numeral][numeral] yielding 26×26×10×10=67,600 different combinations. Even more combinations may be created if distinguishing/using both lower-case and upper-case letters in the same human-readable identifier. In such a case, less than four characters may provide at least 50,000 combinations. For example, a three-letter string may provide 140,608 different combinations ((2×26)×(2×26)×(2×26)) if considering the case form of the letters.

In an embodiment, the characters of the first and second human-readable identifiers are selected from Latin letters and Arabic numerals.

In embodiments, the Latin letters include modern letters commonly used in conjunction with the Latin letters. Thus, in embodiments, by Latin letters is meant the letters used in the English alphabet. The modern English alphabet consists of 26 letters, each having an upper- and lower-case form. Likewise, Arabic numerals consists of ten different characters (0-9). Thus, by combining a single Latin letter (upper-case or lower-case) and a single Arabic numeral yields 26 times 10 different combinations; 260 different combinations. Using multiple Latin letters and/or Arabic numerals yields even more different combinations, thus allowing for a versatile tool when developing a human-readable identifier.

In an embodiment, each of the first and second human-readable identifiers is selected from a combination of characters, a color, a geometric shape, a pie chart icon, and a flat design icon.

Providing a human-readable identifier as a combination of characters provides for creating many different identifiers from a select group of characters (e.g. Latin letters and Arabic numerals).

Providing a human-readable identifier as a color, e.g. a colored dot on the monitor device or by dyeing the entire or parts of the housing of the monitor device, provides for a fast and easy identification.

Providing a human-readable identifier being a geometric shape, a pie chart icon, or a flat design icon provides for a fast and easy identification, since the identifiers may be selected from well-known shapes/icons/symbols.

In embodiments, the first human-readable identifier is of a type/format (character, color, geometric shape, pie chart icon, and flat design icon) different from the type/format of the second human-readable identifier. In embodiments, the first and second human-readable identifiers are of the same type/format.

In an embodiment, the first and second human-readable identifiers are provided by means of engraving, dyeing, or printing on the first and second monitor devices, respectively.

Thereby may the monitor devices be provided with the human-readable identifier at the time of production (e.g., as part of the production line), thereby easing the production line.

In an embodiment, the ostomy system further comprises a server configured to communicate with the accessory device. In an embodiment, the server is configured to obtain the first monitor data and second monitor data from the accessory device, and the server is configured to pool the first monitor data and the second monitor data in a unique user profile. In embodiments, the server is a cloud server configured to communicate wirelessly with the accessory device.

In embodiments, the server comprises a memory and/or a processor. Thereby, certain or all processing power may be provided by the server rather than the accessory device. In embodiments, the server communicates wirelessly, e.g. through an Internet protocol, with the accessory device. In embodiments, data, e.g. monitor data obtained from the monitor device, is transmitted from the accessory device to the server. In embodiments, the server processes the monitor data.

In embodiments, the unique user profile comprises historic data pertaining to a specific user.

Thereby, the at least two monitor devices may be replaced without affecting the historic data. Thus, the historic data comprises pooled data obtained from both current and past monitor devices used by the user.

In a second aspect of the invention, a kit of parts is provided. The kit of parts comprises an ostomy appliance comprising a sensor assembly, at least two monitor devices including a first monitor device having a first human-readable identifier comprising maximally four characters providing at least 50,000 different combinations and a second monitor device having a second human-readable identifier comprising maximally four characters providing at least 50,000 different combinations, each of the at least two monitor devices being configured to collect data from the sensor assembly. Further, the kit of parts comprises an accessory device having a first interface configured to communicate with each of the first and second monitor devices and a user interface configured to receive a user input indicative of the first and/or second human-readable identifier.

It is envisioned that the embodiments disclosed in relation to the first aspect of the invention is applicable to the kit of parts according to the second aspect of the invention. By providing each of the first and second human-readable identifiers as an identifier comprising maximally four characters providing at least 50,000 different combinations (generated at random for each marking of a monitor device, as discussed in relation to the first aspect), the first and second human-readable identifiers may be considered effectively different. Thereby, during manufacturing or packaging of the two monitor devices, the second monitor device may be selected at random from a plurality of monitor devices without the risk of selecting a monitor device having a human-readable identifier identical to the human-readable identifier of the first monitor device.

In a third aspect of the invention, a monitor device for collecting data from a sensor assembly of an ostomy appliance is disclosed. The monitor device comprises a housing. A human-readable identifier is provided on a surface of the housing. The human-readable identifier comprises maximally four characters providing at least 50,000 different combinations.

In embodiments, the characters are selected from Latin letters, including modern letters used in conjunction with Latin letters, and Arabic numerals. For example, the characters are selected from letters of the English alphabet. The English alphabet consists of 26 different letters (A-Z). The Arabic numerals consists of 10 different characters (0-9).

At least 50,000 different combinations by means of maximally four characters can be created through the following combinations of letters from the English alphabet and Arabic numerals (here, only considering a single case form selected from upper-case and lower-case letters):

[letter][letter][letter][letter] yielding 26×26×26×26=456,976 different combinations, [letter][letter][letter][numeral] yielding 26×26×26×10=175,760 different combinations, and [letter][letter][numeral][numeral] yielding 26×26×10×10=67,600 different combinations. Even more combinations may be created if distinguishing/using both lower-case and upper-case letters in the same human-readable identifier. For example, four combinations exist when distinguishing A from a: "AA", "Aa", "aA", and "aa", whereas only one combination exists when not considering case forms: "AA" (or "aa" if using lower-case form throughout).

In embodiments, the characters are selected from additional or other characters, such as Arabic, Greek, and/or Chinese characters, thereby giving rise to even further different combinations capable of providing at least 50,000 different combinations by means of maximally four characters.

Providing at least 50,000 different combinations provides for reducing the need for setting up a smart ordering system taking into account the first human-readable identifier of the first monitor device when packaging and/or shipping the second monitor device having a second human-readable identifier required to be different from the first human-readable identifier according to the aspects of the invention.

Further, providing at least 50,000 different combinations by means of maximally four characters provides for a short and easy-to-remember identifier, whereby it may be considered human-readable.

Further advantages and examples of providing a human-readable identifier according to the third aspect are disclosed in relation to the first and second aspects, which may be considered applicable to the third aspect.

In a fourth aspect of the invention, a method of providing at least two monitor devices is disclosed. The method comprises manufacturing a plurality of monitor devices, each monitor device having a human-readable identifier comprising maximally four characters providing at least 50,000 different combinations, The method further comprises selecting, at random, a first monitor device from the plurality of monitor devices, and selecting, at random, a second monitor device from the plurality of monitor devices, and providing the first monitor device and the second monitor device.

In embodiments, the maximally four characters are provided in a string. In embodiments, the maximally four characters are provided in a matrix.

As a result of manufacturing monitor devices having effectively different human-readable identifiers (due to the at least 50,000 different combinations for the human-readable identifier), a user of an ostomy system can be provided with two monitor devices that the user is able to reliable distinguish; for instance if one has a low battery level and the other is fully charged. In contrast, without the effectively different human-readable identifiers, a user would not be able to distinguish between identical looking monitor devices. As such, a user may not be able to determine which monitor device has a low battery and which monitor device has a full battery. Therefore, the effectively different human-readable identifiers facilitate the human-machine interaction by making it easy for the user to input to the ostomy system which devices are available, and by allowing the system to easily identify to the user the status of each device.

In embodiments, the step of manufacturing a plurality of monitor devices comprises manufacturing at least 50,000 monitor devices as part of a production line, each having a human-readable identifier being different from any other human-readable identifier of the at least 50,000 monitor devices. In embodiments, the human-readable identifiers follow the same format, such as [letter][letter][numeral][numeral], such that the production line can manufacture monitor devices having sequential human-readable identifiers according to the same format. For example, the production line comprises manufacturing a first monitor device and marking it with the first human readable identifier "AA00", followed by manufacturing a second monitor device and marking it with the second human-readable identifier "AA01", and so on. In the end of the production line, the at least 50,000 monitor devices can be pooled and at least two monitor devices can be picked/selected at random and packaged as part of an ostomy system according to the first and second aspect of the invention. Thereby, it is ensured that the two monitor devices picked at random have different (mutually unique) human-readable identifiers.

In embodiments, the monitor devices contained in the plurality of monitor devices may change between selecting the first and second monitor device without departing from the scope. In other words, the production line may continue manufacturing monitor devices between the selection of a first and second monitor device without such continued or intermediate manufacturing will affect the likelihood of selecting an identical human-readable identifier.

In an embodiment, the step of manufacturing a plurality of monitor devices comprises randomly generating a human-readable identifier for each monitor device of the plurality of monitor devices, the human readable identifier comprising maximally four characters providing at least 50,000 different combinations and marking the human-readable identifier on a surface of the respective monitor device.

Thus, in embodiments, the production line may be adapted to generate a human-readable identifier at random (within the given constraints; e.g., maximally four characters providing at least 50,000 different combinations), for each monitor device of the plurality of monitor devices.

In an embodiment, the step of providing the first monitor device and the second monitor device comprises packaging the first monitor device and the second monitor device. Thus, by providing may be meant packaging a first monitor device and a second monitor device. Upon packaging, the first and second monitor devices may be provided (e.g., shipped) to the user.

In an alternative embodiment, the first monitor device is provided (e.g., packaged and shipped) to a user prior to providing (e.g., packaging and shipping) the second monitor device (e.g., the second monitor device is provided upon request from a user or HCP). In such an embodiment, the method of providing at least two monitor devices for an ostomy system may comprise the steps of:

manufacturing a plurality of monitor devices, each monitor device having a human-readable identifier comprising maximally four characters providing at least 50,000 different combinations;

selecting, at random, a first monitor device from the plurality of monitor devices;

providing the first monitor device;

and, in accordance with receiving a request for a second monitor device; selecting, at random, a second monitor device from the plurality of monitor devices; and providing the second monitor device.

For example, the request for a second monitor device may be through a correspondence between a user and a supplier. In embodiments, the monitor devices contained in the plurality of monitor devices may change between selecting the first and second monitor device without departing from the scope. In other words, the production line may continue manufacturing monitor devices between the selection of a first and second monitor device without such continued or intermediate manufacturing will affect the likelihood of selecting an identical human-readable identifier.

The previous embodiments and examples illustrate the need for providing at least two monitor devices having different human-readable identifiers: if a user were to be provided two (identical) monitor devices having identical human-readable identifiers, he/she would be unable to distinguish the monitor devices. However, the task of providing at least two monitor devices having different human-readable identifiers requires certain considerations to be made by the supplier. One such consideration includes how to make sure the ostomy system according to previous embodiments indeed comprises at least two monitor devices having different human-readable identifiers.

By using a human-readable identifier providing for at least 50,000 different combinations, the supplier can select any two or more monitor devices at random from a plurality of monitor devices for a given ostomy system with a minimal risk of selecting two monitor devices having identical human-readable identifiers. In other words, when the human-readable identifier provides for at least 50,000 different combinations, the chances of selecting two monitor devices having identical human-readable identifiers is close to zero ($\frac{1}{50,000}$), and the human-readable identifiers may as such be considered effectively different. Thereby, a reduced need to set up a system capable of selecting a second monitor device having a certain human-readable identifier different from a previously-selected first monitor device having a certain human-readable identifier is provided. In other words, when the number of different possible combinations of the human-readable identifiers is sufficiently high, e.g. 50,000, the supplier can select the second monitor device at random, without considering the identifier of the first monitor device.

In an embodiment, the characters of the first and second human-readable identifiers are selected from Latin letters and Arabic numerals.

In embodiments, the Latin letters include modern letters commonly used in conjunction with the Latin letters. Thus, in embodiments, by Latin letters is meant the letters used in the English alphabet. The modern English alphabet consists of 26 letters, each having an upper- and lower-case form. Likewise, Arabic numerals consists of ten different characters (0-9). Thus, by combining a single Latin letter and a single Arabic numeral yields 26 times 10 different combinations; 260 different combinations. Using multiple Latin letters, differentiating/distinguishing between upper-case and lower-case, and/or Arabic numerals yield even more different combinations, thus allowing for a versatile tool/format when developing a human-readable identifier.

In embodiments, each of the first and second human-readable identifiers is selected from a combination of characters, a color, a geometric shape, a pie chart icon, and a flat design icon.

Providing a human-readable identifier as a combination of characters provides for creating many different identifiers from a select group of characters (e.g. Latin letters and Arabic numerals).

Providing a human-readable identifier as a color, e.g. a colored dot on the monitor device or by dyeing the entire or parts of the housing of the monitor device, provides for a fast and easy identification.

Providing a human-readable identifier being a geometric shape, a pie chart icon, or a flat design icon provides for a fast and easy identification, since the identifiers may be selected from well-known shapes/icons/symbols.

In embodiments, the first human-readable identifier is of a type (character, color, geometric shape, pie chart icon, and flat design icon) different from the type of the second human-readable identifier. In embodiments, the first and second human-readable identifiers are of the same type.

In an embodiment, marking the first monitor device and the second monitor device with the first and second human-readable identifiers, respectively, comprises engraving, dyeing, or printing.

Thereby may the monitor devices be provided with the human-readable identifier at the time of production, thereby easing the production line.

DETAILED DESCRIPTION OF THE DRAWINGS

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone/smartphone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 can be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data. Based on the processed ostomy data, the monitor device 6 may determine what monitor data that are transmitted to the accessory device 8. In the illustrated ostomy system, the accessory device 8 is a mobile phone, however the accessory device 8 can be embodied as another handheld device, such as a tablet device, or a wearable, such as a watch or other wrist-worn electronic device.

Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a centre point 19. The size and/or shape of the stomal opening 18 is typically adjusted by the user or nurse before application of the ostomy appliance to accommodate the user's stoma.

The ostomy system 1 optionally comprises a docking station 20 forming an alternative/additional accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

According to certain embodiments, the ostomy system 1 comprises a first monitor devices 6 and a second monitor device (not shown). The monitor devices 6 are interchangeable and can perform the same functions. The monitor devices 6 also look identical, but the user must be able to reliably distinguish between the two monitor devices, for instance if one has a low battery level and the other is fully charged. The present invention solves this by providing on each monitor device 6 a unique human-readable identifier 26, for instance in the form of a symbol or a combination of characters, as discussed in more detail below. This facilitates the human-machine interaction by making it easy for the user to input to the accessory device 8 which monitor devices 6 are available, and by allowing the system 1 to easily identify to the user the status of each monitor device 6.

Figure 2:
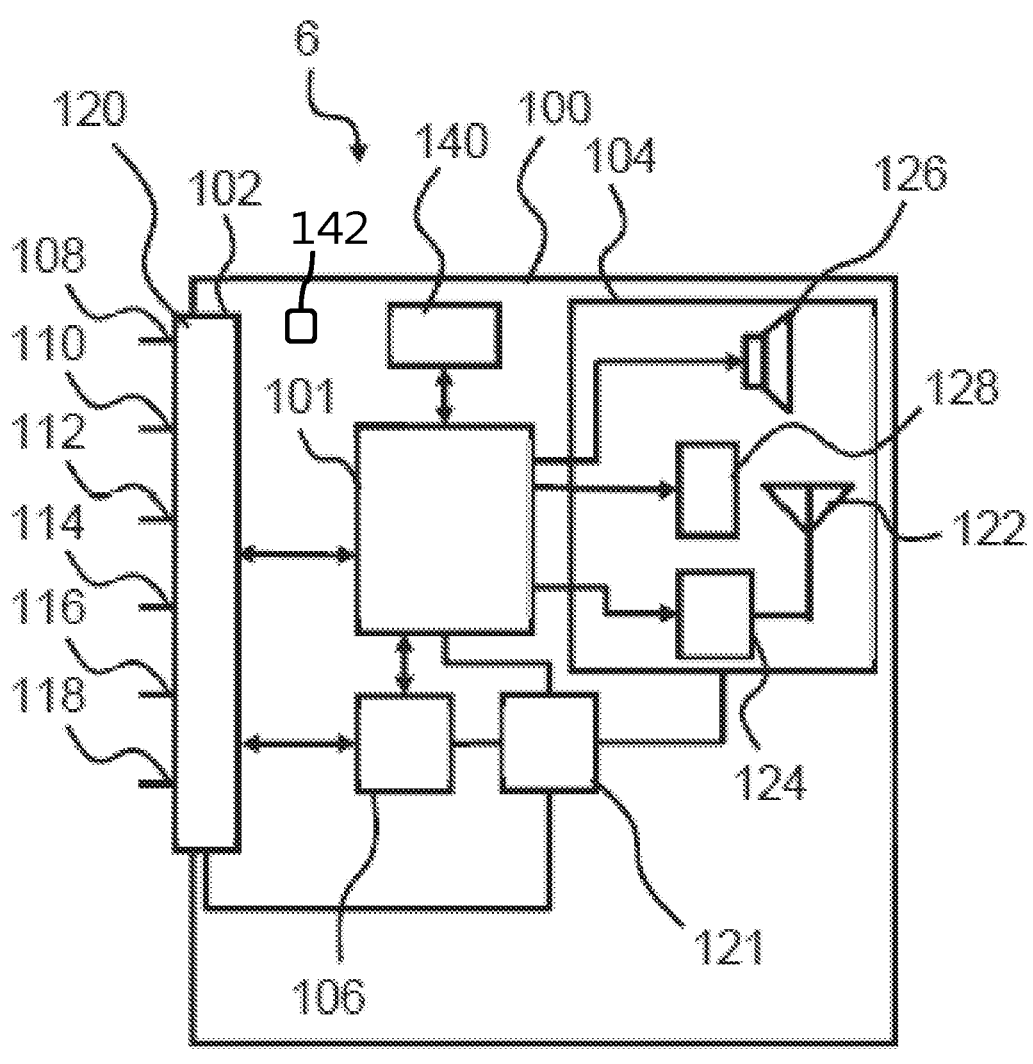
FIG. 2 illustrates an exemplary monitor device of the ostomy system.

FIG. 2 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102. On a surface of the housing 100, a human-readable identifier is provided according to the present disclosure.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery, such as a rechargeable battery, and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user. The monitor device 6 may comprise a 3-axis accelerometer 142 connected to the processor 101.

The processor 101 is configured to apply a processing scheme, and the first interface 102 (appliance interface) is configured for collecting ostomy data from the base plate and/or the sensor patch coupled to the first interface, the ostomy data comprising leakage ostomy data from leakage electrodes of the ostomy appliance. The ostomy data optionally comprises first ostomy data from a first electrode pair of the base plate and/or the sensor patch, second ostomy data from a second electrode pair of the base plate and/or the sensor patch, and/or third ostomy data from a third electrode pair of the base plate and/or the sensor patch. The ostomy data can be stored in the memory 106 and/or processed in the processor 101 in order to obtain parameter data. The parameter data can be stored in the memory 106. The processor 101 is configured to apply a processing scheme, wherein to apply a processing scheme comprises obtaining primary leakage parameter data based on primary leakage ostomy data; obtaining secondary leakage parameter data based on secondary leakage ostomy data; and obtaining tertiary leakage parameter data based on tertiary leakage ostomy data. Optionally the processing scheme comprises obtaining first parameter data based on the first ostomy data; obtaining second parameter data based on the second ostomy data; obtaining third parameter data based on the third ostomy data. In other words, the processor 101 can be configured to obtain first, second and third parameter data based on respective first, second and third ostomy data. To apply a processing scheme comprises to determine an operating state of the base plate and/or the sensor patch of the ostomy appliance based on one or more, e.g. all, of primary leakage parameter data, secondary leakage parameter data, and tertiary leakage parameter data, wherein the operating state is indicative an acute leakage risk in a sensing zone for the ostomy appliance. The monitor device 6 is configured to, in accordance with a determination that the operating state is a primary leakage operating state, transmit a primary leakage monitor signal comprising monitor data indicative of the primary leakage operating state of the base plate and/or the sensor patch via the second interface; and in accordance with a determination that the operating state is a secondary leakage operating state, transmit a secondary leakage monitor signal comprising monitor data indicative of the secondary leakage operating state of the base plate and/or the sensor patch via the second interface. The monitor device 6 can be configured to, in accordance with a determination that the operating state is a tertiary leakage operating state, transmit a tertiary leakage monitor signal comprising monitor data indicative of the tertiary leakage operating state of the base plate and/or the sensor patch via the second interface.

Figure 3:
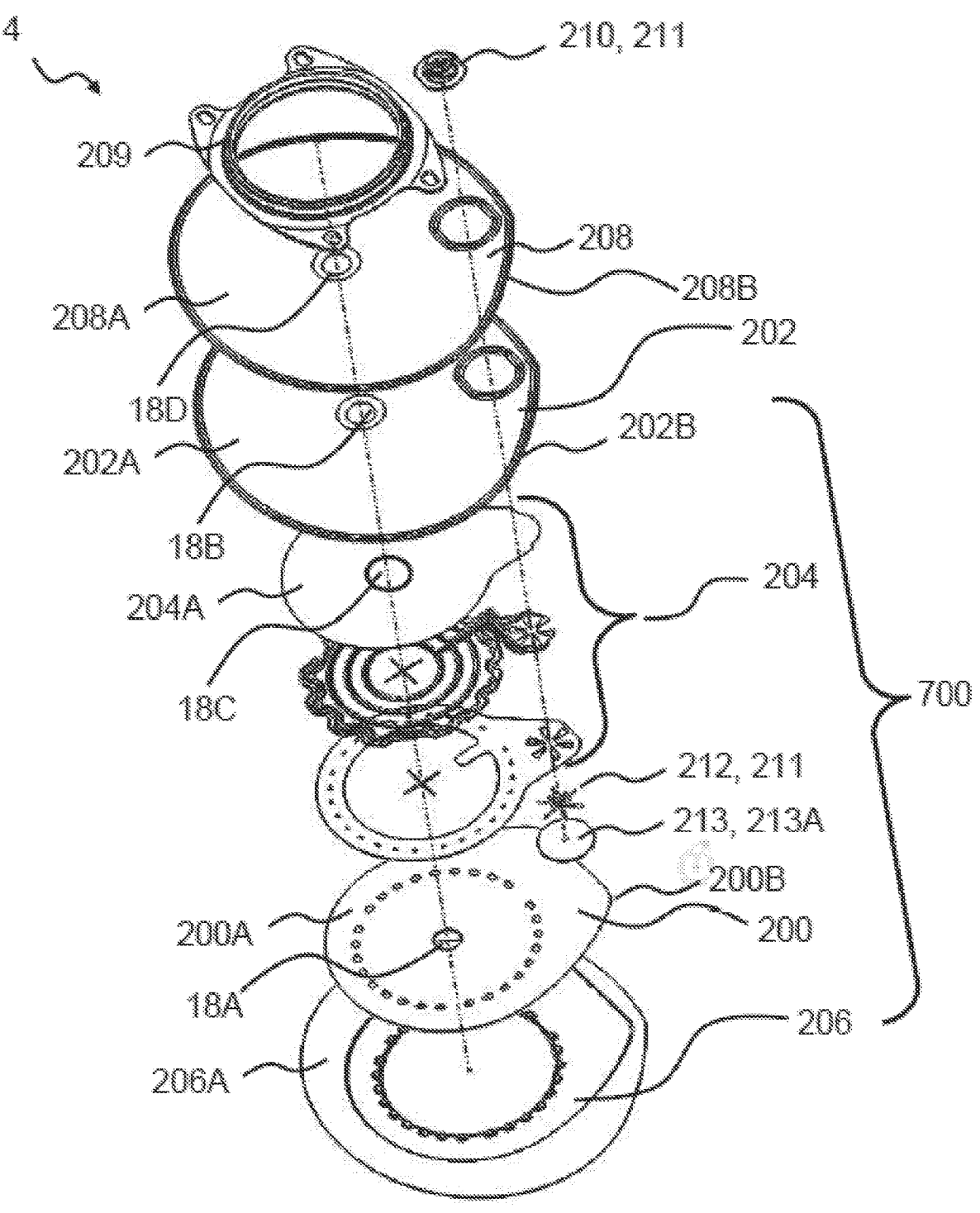
FIG. 3 illustrates an exploded view of a base plate of an ostomy appliance.

FIG. 3 illustrates an exploded view of an exemplary base plate of an ostomy appliance. The base plate 4 comprises a first adhesive layer 200 with a stomal opening 18A. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer, with a stomal opening 18B. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with stomal opening 18C and electrodes formed on a proximal surface of the support layer. The base plate 4 comprises a release liner 206 that is peeled off by the user prior to applying the base plate 4 on the skin. The base plate 4 comprises a top layer 208 with a stomal opening 18D and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, can be provided as a separate patch to be applied to an existing base plate, e.g. comprising one or more of the components as described, such as to provide a base plate like the base plate 4 as described. For example, a sensor patch 700 can be provided, e.g. comprising the electrode assembly 204, the first connector 211, the first intermediate element 213, the first adhesive layer 200 and the release liner 206. Additionally, the sensor patch 700 can also comprise the second adhesive layer 202 and/or the top layer 208. It may be envisioned that the user can provide a hole in layers of the base plate whereto the sensor patch 700 is to be applied, to allow for the first connector 211 of the sensor patch 700 to protrude through layers of the base plate whereto the sensor patch 700 is applied. Alternatively, the sensor patch 700 can be applied to the base plate such that the first connector 211 is positioned outside the periphery of the base plate.

Figure 4:
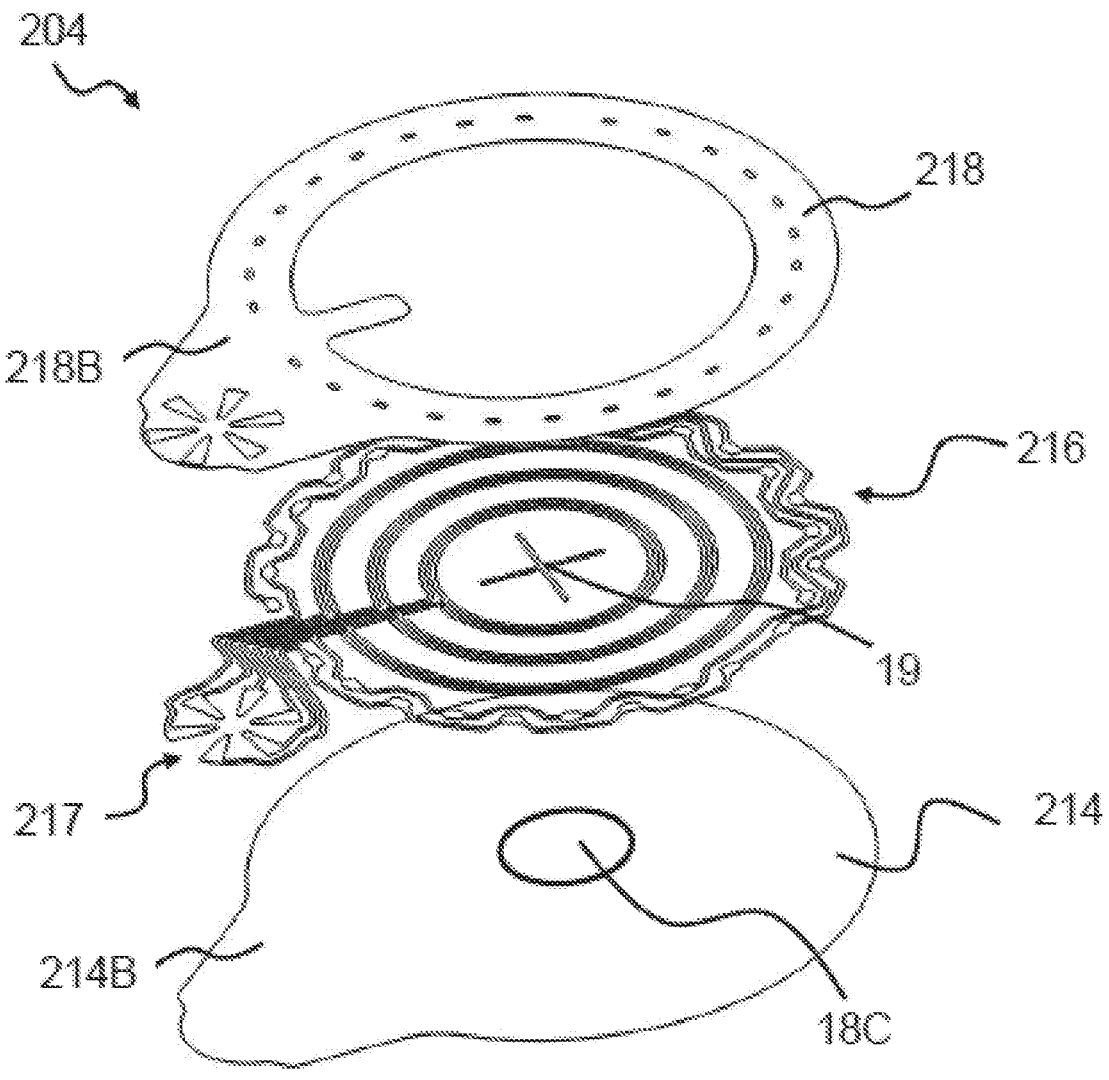
FIG. 4 illustrates an exploded view of an exemplary electrode assembly.

FIG. 4 illustrates an exploded view of an exemplary electrode assembly 204 of a base plate and/or sensor patch. The electrode assembly 204 has a distal side 204A and a proximal side 204B. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are positioned and/or formed on a proximal side 214B of the support layer 214. Further, electrode assembly 204 comprises a masking element 218 with proximal surface 218B and configured to insulate electrode parts of electrodes 216 from the first adhesive layer of the base plate and/or the sensor patch. The masking element 218 covers or overlap with parts of the electrodes 216 when seen in the axial direction.

Figure 5:
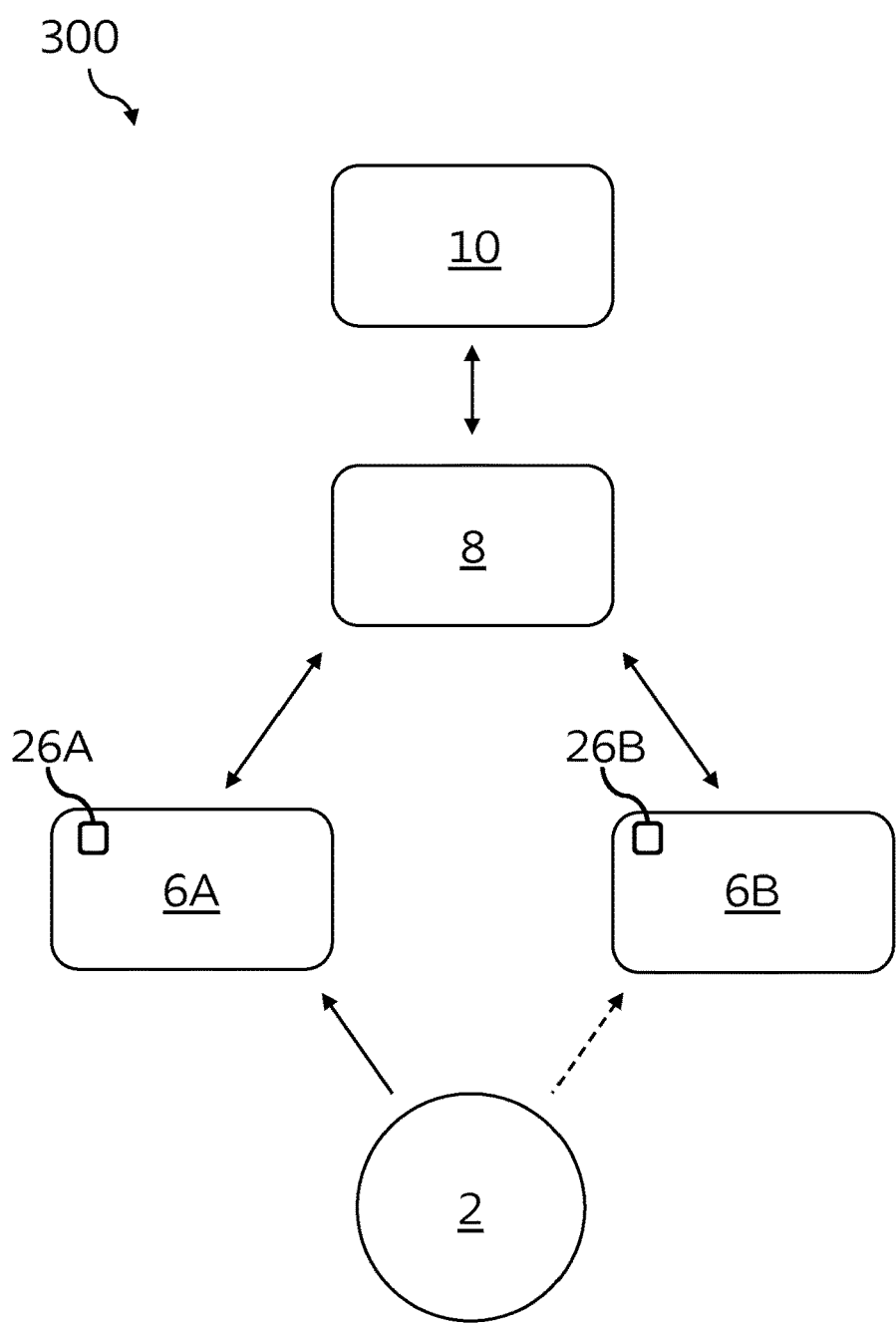
FIG. 5 illustrates an exemplary ostomy comprising two monitor devices.

FIG. 5 illustrates an ostomy system 300 comprising two monitor devices 6A, 6B. As set forth above, one of the monitor devices 6A, 6B can be coupled to the ostomy appliance 2, while the other monitor device is decoupled from the ostomy appliance 2. For example, the first monitor device 6A may be coupled to the ostomy appliance 2 and the second monitor device 6B may be decoupled from the ostomy appliance 2 (illustrated by the dashed arrow). When the first monitor device 6A is coupled to the ostomy appliance 2, said monitor device 6A may be collecting data from the ostomy appliance 2, as set forth above. According to certain embodiments, the second monitor device 6B may be coupled to the docking station 20 (FIG. 1) and charging when said second monitor device 6B is decoupled from the ostomy appliance 2 or the second monitor device 6B may be decoupled from the docking station 20 and ready for use in the event the battery of the first monitor device 6A is low.

To distinguish between the two monitor devices 6A, 6B, each of monitor devices 6A, 6B includes different, respective human-readable identifiers 26A, 26B. The human-readable identifiers 26A, 26B allow a user to distinguish between the monitor devices 6A, 6B for the reasons explained above.

In embodiments, the accessory device 8 includes a user interface that allows a user to create profiles for each of the monitor devices 6A, 6B. The profiles may include an identifier that corresponds to the human-readable identifier 26A, 26B located on the monitor device 6A, 6B so that the user can distinguish between which of the monitor devices 6A, 6B the user is selecting on the user interface of the accessory device 8. On the contrary, if the human-readable identifiers 26A, 26B were not included on the monitor devices 6A, 6B, a user may not be able to determine which of the two monitor devices 6A, 6B to select on the user interface of the accessory device 8. As a result, a user may not be able to determine whether one of the monitor devices 6A, 6B is malfunctioning or whether the monitor device 6A, 6B is not the monitor device that has been selected.

When a monitor device, e.g., monitor device 6A, is selected, the accessory device 8 can send a signal to the selected monitor device 6A indicating that it has been selected. In response to receiving a signal that the monitor device 6A has been selected, the selected monitor device 6A may transmit its operating status to the accessory device 8. The operating status of the monitor device 6A may indicate the battery level of the monitor device 6A and/or a data collection mode of the monitor device 6A.

The operating status can be displayed on the user interface of the accessory device 8 so that a user can determine the remaining battery of the monitor device 6A, 6B and/or whether the monitor device 6A, 6B is collecting data from the ostomy appliance 2.

Additionally, or alternatively, in response to receiving a signal that the monitor device 6A, 6B has been selected, the selected monitor device 6A, 6B may transmit the collected data from the ostomy appliance 2 to the accessory device 8, which in turn can transmit it to a server 10 and/or receive collected data from the server 10.

In embodiments, the monitor device 6A, 6B may only transmit the collected data in response to a user requesting the collected data be transmitted via a selection on the user interface to transmit the collected data. Further, by transmitting collected data to the accessory device 8 only when a user selects the monitor device 6A, 6B, the monitor device 6A, 6B can save valuable battery power that otherwise would be expended in the event the monitor device 6A, 6B was constantly transmitting data or transmitting data on an intermitted basis. As such, including the different, respective human-readable identifiers 26A, 26B on the monitor devices 6A, 6B allows a user to select a monitor device 6A, 6B without guessing and can lead to battery savings.

In embodiments, because only one of the monitor devices 6A, 6B is coupled to the ostomy appliance 2 during an instant in time, the accessory device 8 and/or the server 10 may combine and/or pool the data received from the monitor devices 6A, 6B to form a string of collected data. To do so, the data collected by the monitor devices 6A, 6B may be timestamped and ordered by the accessory device 8 and/or the server 10 according to the time stamps of the collected data. Thereby, a coherent/continuous data set can be formed in order to generate a continuous picture of the user's use of the ostomy appliance.

In exemplary ostomy systems, the ostomy system is used in a health care facility where the accessory device is configured to communicate with a plurality of data collecting monitor devices at once (one for each user/wearer). Thereby, a health care professional or user is capable of receiving notifications, such as notifications indicating a leakage, from a plurality of monitor devices—each belonging to a certain user. The provision of a human-readable identifier on the monitor device and on the associated user interface of the accessory device provides for identifying the monitor device, and as such the user wearing the monitor device, such that the health care professional can institute appropriate actions, e.g. changing the ostomy appliance associated with the monitor device.

Figure 6A:
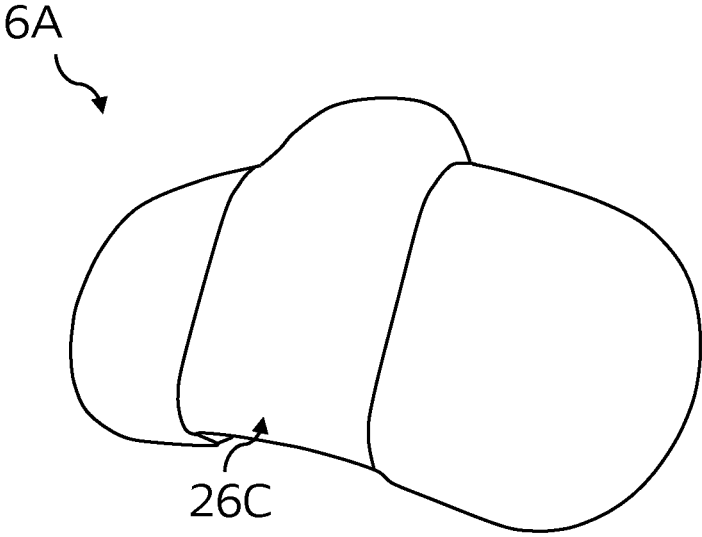
FIG. 6A illustrates a perspective view of a distal surface of a first exemplary monitor device having a first human-readable identifier.
Figure 6B:
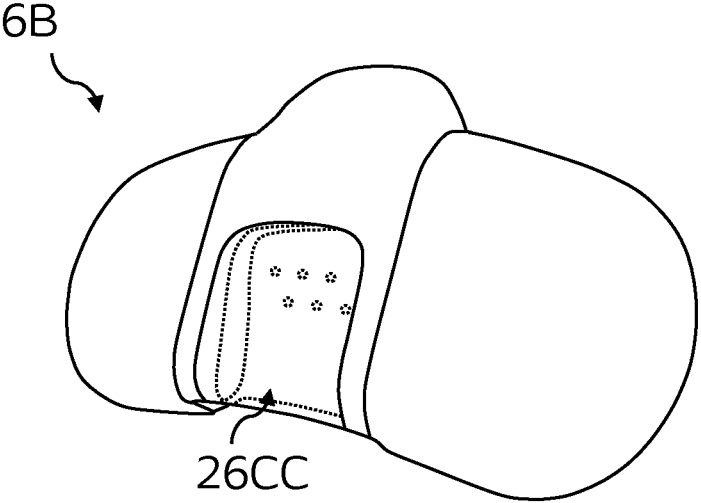
FIG. 6B illustrates a perspective view of a distal surface of a second exemplary monitor device having a second human-readable identifier.

FIG. 6A is a perspective view of a distal surface of a first exemplary monitor device 6A having a first human-readable identifier 26C; FIG. 6B illustrates a perspective view of a distal surface of a second exemplary monitor device 6B having a second human-readable identifier 26CC. A user may be provided with both monitor devices 6A, 6B so that one monitor device 6A, 6B can be in use and the other monitor device 6A, 6B can be recharged as set forth above. The monitor devices 6A, 6B are interchangeable and can perform the same functions. However, the first monitor device 6A includes a different human-readable identifier 26C than the human-readable identifier 26CC of the second monitor device 6B. By being able to readily distinguish between the two monitor devices 6A, 6B, a user may select which of the two monitor devices 6A, 6B to connect to via a user interface on an accessory device 8.

In the illustrated embodiment, the first human-readable identifier 26C includes an opaque portion on a distal surface of the first monitor device 6A whereas the second human-readable identifier 26CC includes a translucent or transparent portion on a distal surface of the second monitor device 6B. As such, a user can readily identify and distinguish between the first monitor device 6A and the second monitor device 6B via the first human-readable identifier 26C and the second human-readable identifier 26CC.

The first human-readable identifier 26C and the second human-readable identifier 26CC may be different colours. In these embodiments, the first human-readable identifier 26C and the second human-readable identifier 26CC may both be opaque, translucent, or transparent.

Including a human-readable identifier 26C, 26CC on a distal surface of the monitor devices 6A, 6B allows a user to identify which of the two monitor devices 6A, 6B to connect to the accessory device when the monitor device is coupled to an ostomy appliance 2. That is, the proximal surface of the monitor device 6A, 6B may face the skin of the user when the monitor device 6A, 6B is coupled to the ostomy appliance 2. As such, it may be difficult for a user to view the proximal surface of the monitor device 6A, 6B. Including the human-readable identifier 26C, 26CC on a distal surface of the monitor devices 6A, 6B solves this problem.

Figure 7:
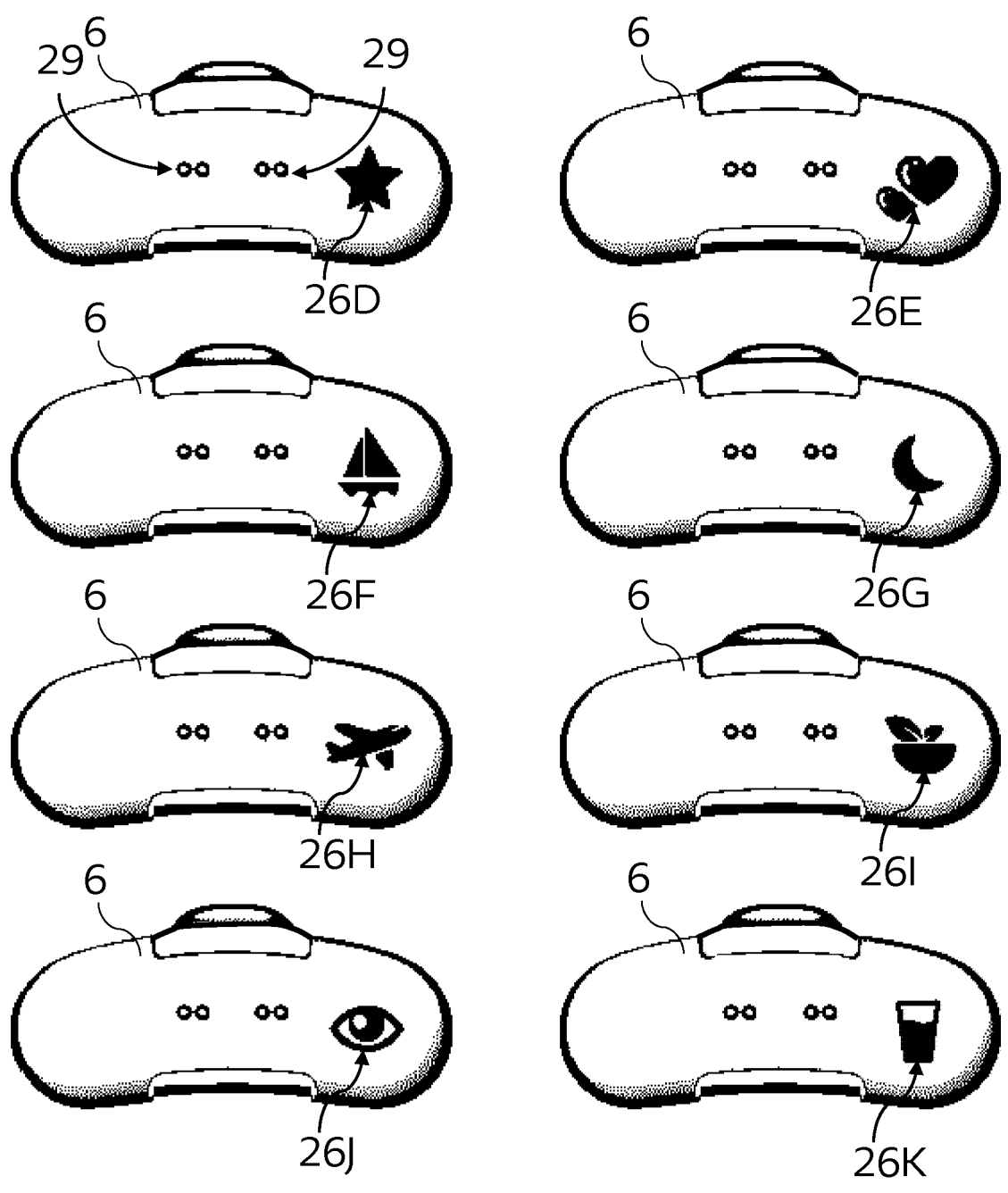
FIG. 7 illustrates exemplary flat design icons as human-readable identifiers on a proximal surface of a monitor device.

FIG. 7 illustrates exemplary flat design icons 26D-26K as human-readable identifiers on a proximal surface of a monitor device 6. An advantage to including a flat design icons 26D-26K in comparison to other types of human-readable identifiers is that a user may be less likely to confuse one of the flat design icons 26D-26K for another flat design icon 26D-26K.

As illustrated, the flat design icons 26D-26K may be located on a proximal side of the monitor device 6. Additionally, or alternatively, the flat design icons 26D-26K may be on a distal surface of the monitor device 6. While there is only one flat design icon 26D-26K illustrated on the monitor device 6, there may be more than one flat design icon 26D-26K on a monitor device 6. Further, while the flat design icons 26D-26K are illustrated as being located to the right of the charging terminals 29, the flat design icons 26D-26K may be located above the charging terminals 29, below the charging terminals 29, to the left of the charging terminals 29, and/or diagonally the charging terminals 29.

As illustrated, examples of flat design icons 26D-26K include, but are not limited to, one or more stars 26D, one or more hearts 26E, one or more boats 26F, one or more half-moons 26G, one or more airplanes 26H, one or more plants 26I, one or more facial features 26J (e.g., one or more eyes, one or more mouths, etc.), and/or one or more beverages 26K.

Figure 8:
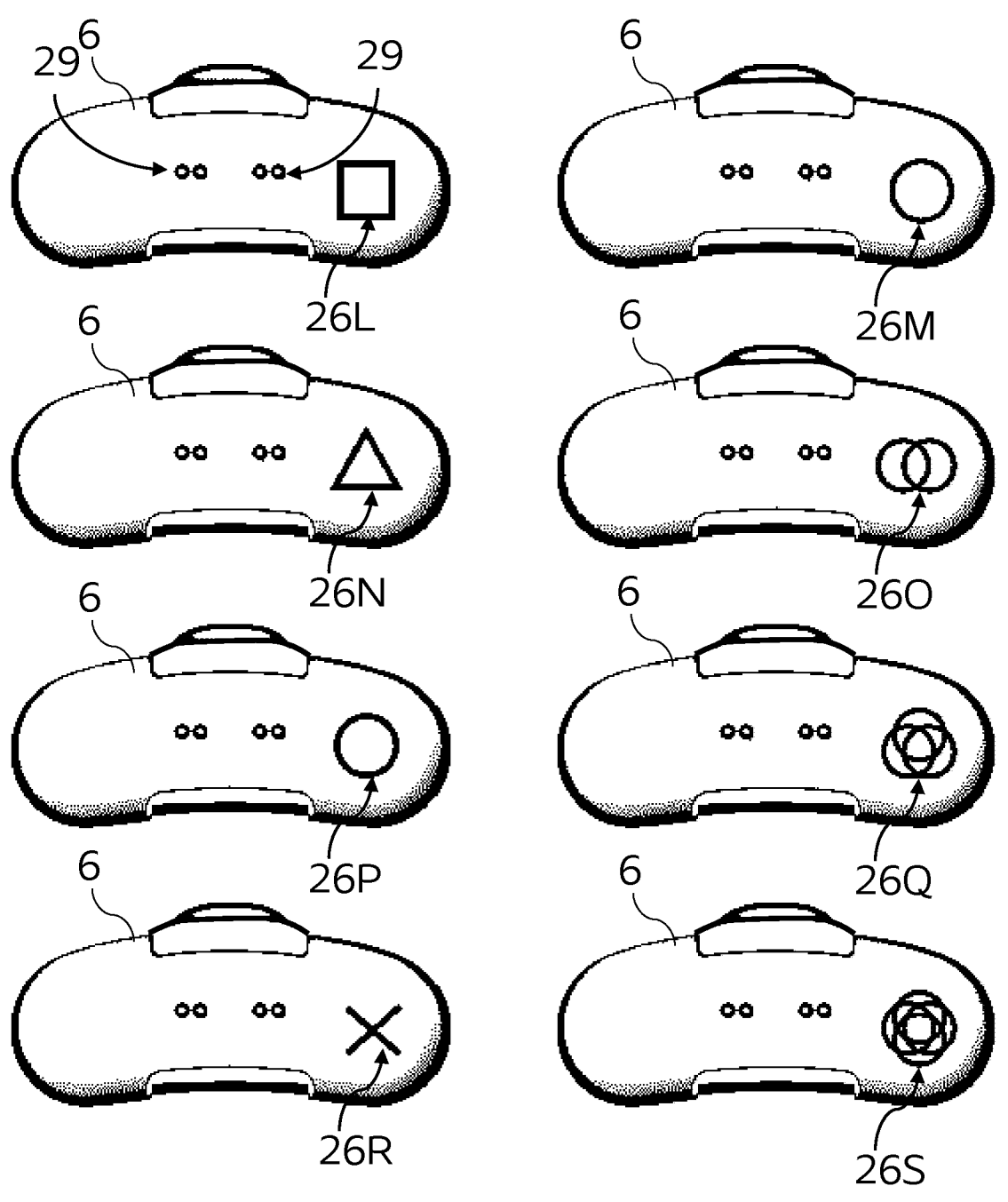
FIG. 8 illustrates exemplary geometric shapes as human-readable identifiers on a proximal surface of a monitor device.

FIG. 8 illustrates other exemplary geometric shapes 26L-26S as human-readable identifiers on a proximal surface of a monitor device 6. Additionally, or alternatively, the geometric shapes 26L-26S may be on a distal surface of the monitor device 6. While there is only one geometric shape 26L-26S illustrated on the monitor device 6, there may be more than one geometric shape 26L-26S on a monitor device 6. Further, while the geometric shapes 26L-26S are illustrated as being located to the right of the charging terminals 29, the geometric shapes 26L-26S may be located above the charging terminals 29, below the charging terminals 29, to the left of the charging terminals 29, and/or diagonally the charging terminals 29.

As illustrated, examples of geometric shapes 26L-26S include, but are not limited to, one or more squares 26L, one or more circular rings 26M, one or more triangles 26N, two intersecting rings arranged side-by-side 26O, one or more ovular rings 26P, three intersecting rings 26Q, one or more x's or crosses 26R, and/or four intersecting rings 26S.

Figure 9:
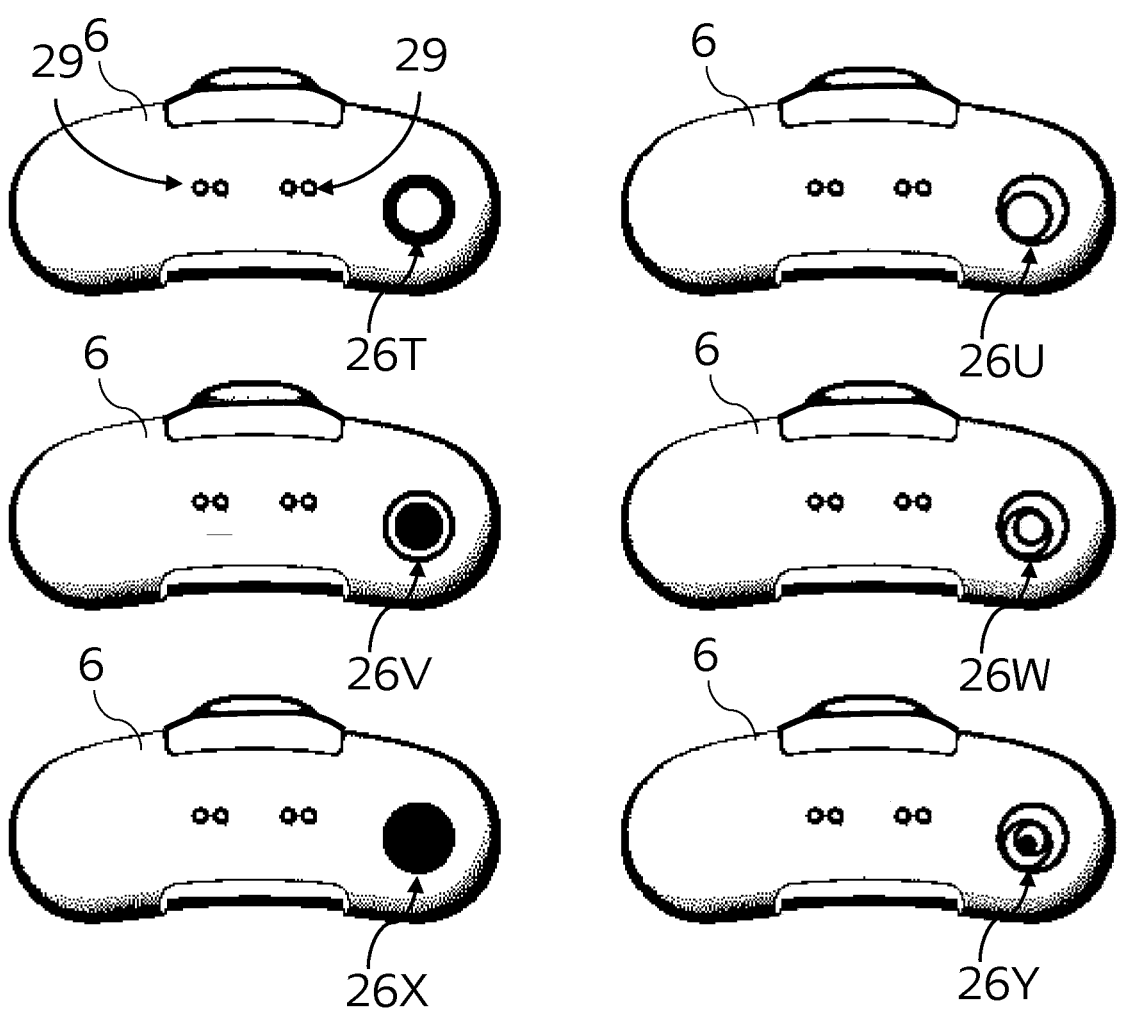
FIG. 9 illustrates other exemplary geometric shapes as human-readable identifiers on a proximal surface of a monitor device.

FIG. 9 illustrates other exemplary geometric shapes 26T-26Y as human-readable identifiers on a proximal surface of a monitor device 6. As illustrated, the geometric shapes 26T-26Y include, but are not limited to, one or more rings 26T having a thicker perimeter than the ring 26M, one ring inside another ring 26U, a solid circle inside a ring 26V, a first ring inside a second ring inside a third ring 26W, one or more solid circles 26X, and/or a first ring inside a second ring inside a third ring inside a fourth ring 26Y.

Figure 10:
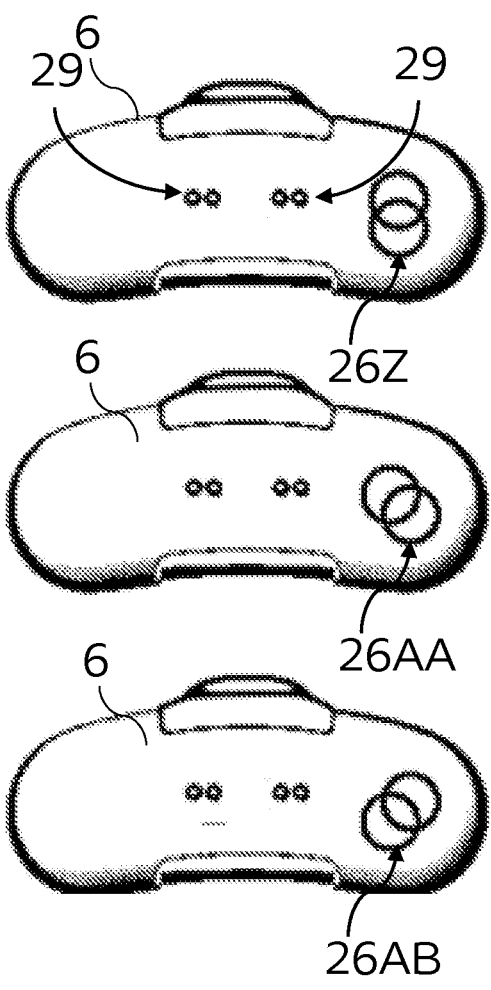
FIG. 10 illustrates even other exemplary geometric shapes as human-readable identifiers on a proximal surface of a monitor device.

FIG. 10 illustrates even other exemplary geometric shapes 26Z-26AB as human-readable identifiers on a proximal surface of a monitor device 6. As illustrated, the geometric shapes 26Z-26AB include, but are not limited to, two intersecting rings arranged in an over-under relationship 26Z, two intersecting rings arranged in a descending diagonal relationship 26AA and/or two intersecting rings arranged in an ascending diagonal relationship 26AB.

Figures 11, 12:
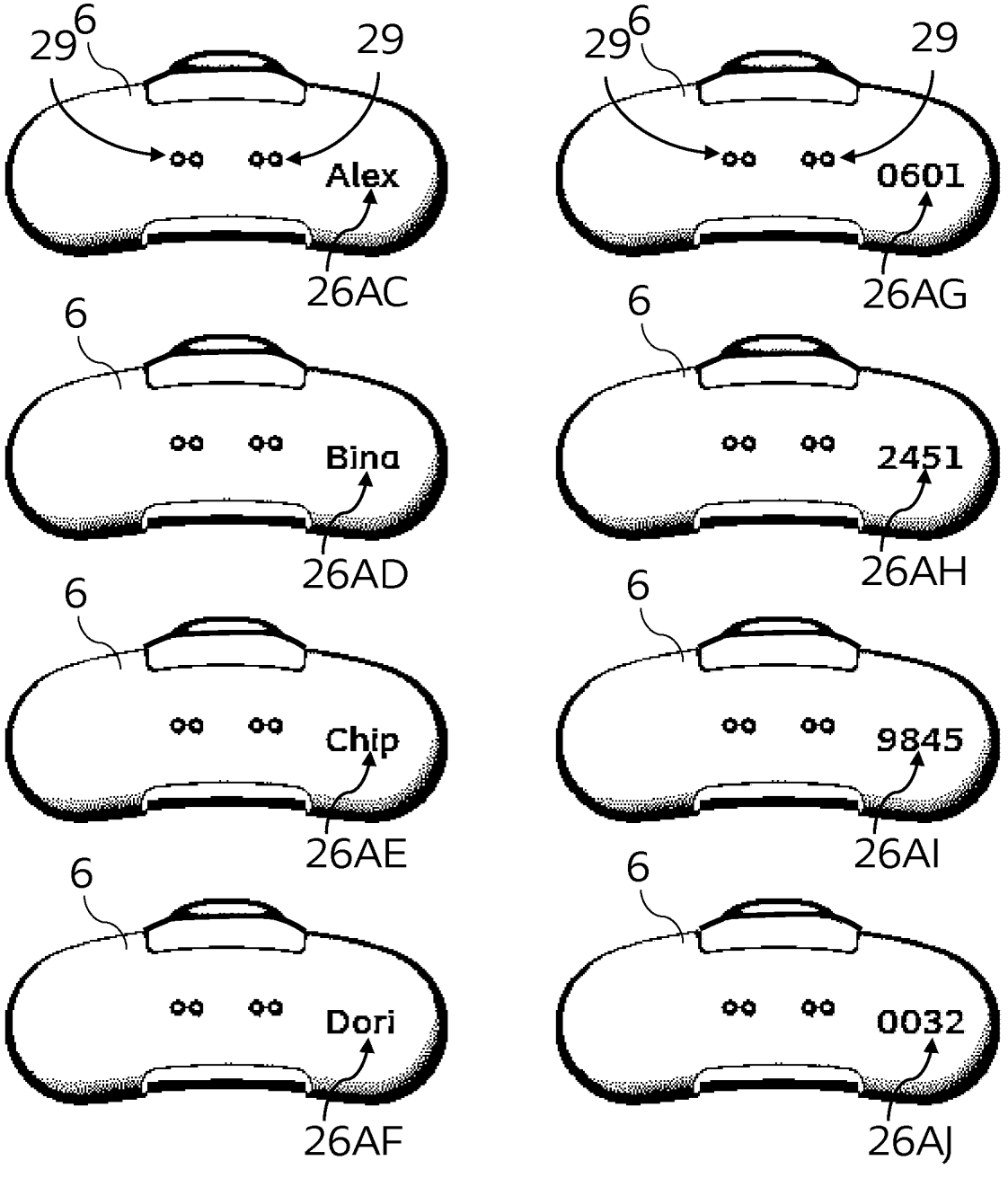
FIG. 11 illustrates exemplary names as human-readable identifiers on a proximal surface of a monitor device.
FIG. 12 illustrates exemplary numeric strings as human-readable identifiers on a proximal surface of a monitor device.

FIG. 11 illustrates exemplary names 26AC-26AF as human-readable identifiers on a proximal surface of a monitor device 6. As illustrated, the names 26AC-26AF may be limited to four letters. As such, in embodiments, the first four letters of a user's first name may be used as the human-readable identifier on a first monitor device 6 and the first four letters of a user's last name may be used as the human-readable identifier on a second monitor device 6.

In embodiments, the names 26AC-26AF may be located on a proximal side of the monitor device 6. Additionally, or alternatively, the names 26AC-26AF may be on a distal surface of the monitor device 6. While the names 26AC-26AF are illustrated as being located to the right of the charging terminals 29, the names 26AC-26AF may be located above the charging terminals 29, below the charging terminals 29, to the left of the charging terminals 29, and/or diagonally the charging terminals 29.

FIG. 12 illustrates exemplary numeric strings 26AG-26AJ as human-readable identifiers on a proximal surface of a monitor device 6. As illustrated, the numeric strings 26AG-26AJ may include four Arabic numerals consisting of ten different characters (0-9). However, in other embodiments, the numeric strings 26AG-26AJ may have more than four characters or fewer than four characters.

In embodiments, the numeric strings 26AG-26AJ may be located on a proximal side of the monitor device 6. Additionally, or alternatively, the numeric strings 26AG-26AJ may be on a distal surface of the monitor device 6. While the numeric strings 26AG-26AJ are illustrated as being located to the right of the charging terminals 29, the numeric strings 26AG-26AJ may be located above the charging terminals 29, below the charging terminals 29, to the left of the charging terminals 29, and/or diagonally the charging terminals 29.

Figure 13:
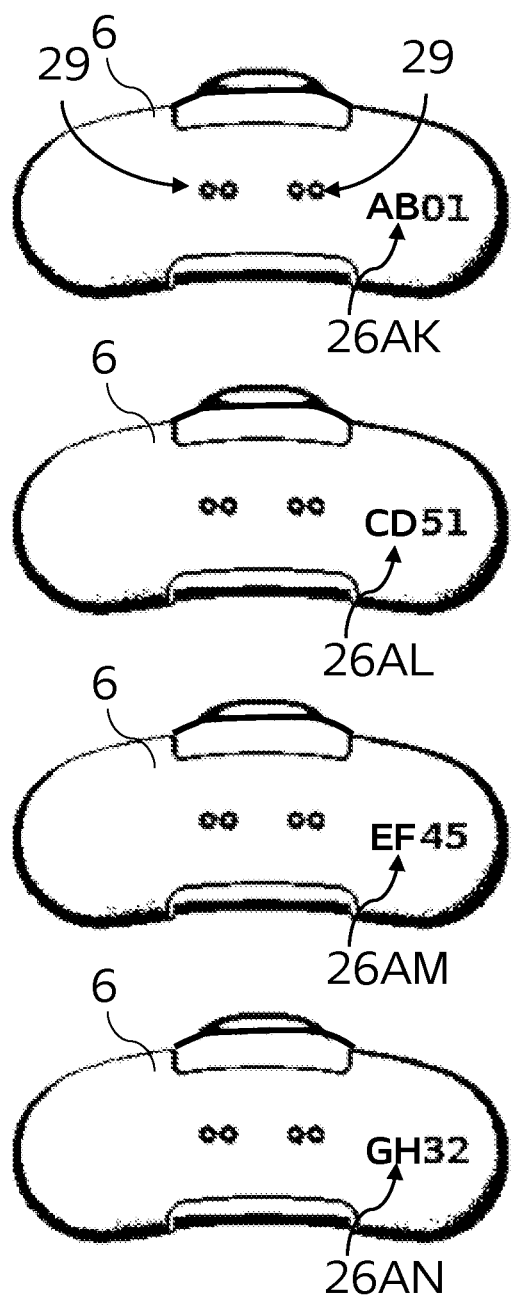
FIG. 13 illustrates exemplary alpha-numeric strings as human-readable identifiers on a proximal surface of a monitor device.

FIG. 13 illustrates exemplary alpha-numeric strings 26AK-26AN as human-readable identifiers on a proximal surface of a monitor device 6. As illustrated, the alpha-numeric strings 26AK-26AN may include two Latin letters consisting of 26 characters (A-Z) followed by two Arabic numerals consisting of ten different characters (0-9). However, in other embodiments, the alpha-numeric strings 26AK-26AN may have more than four characters, fewer than four characters, more than two Latin letters, fewer than two Latin letters, more than two Arabic numerals, or fewer than two Arabic numerals.

In embodiments, the numeric strings 26AK-26AN may be located on a proximal side of the monitor device 6. Additionally, or alternatively, the numeric strings 26AK-26AN may be on a distal surface of the monitor device 6. While the numeric strings 26AK-26AN are illustrated as being located to the right of the charging terminals 29, the numeric strings 26AK-26AN may be located above the charging terminals 29, below the charging terminals 29, to the left of the charging terminals 29, and/or diagonally the charging terminals 29.

Figures 14, 15:
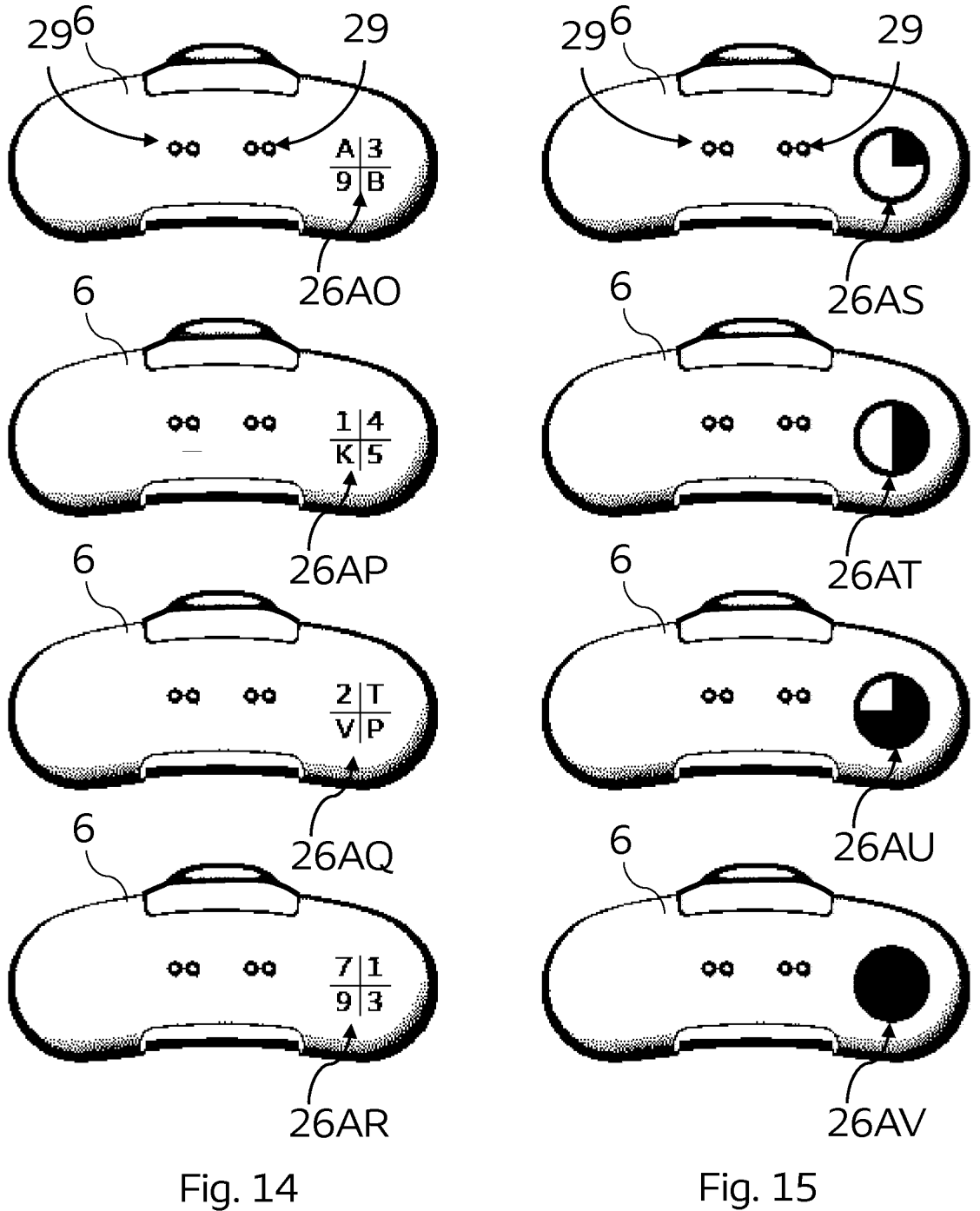
FIG. 14 illustrates exemplary character matrices as human-readable identifiers on a proximal surface of a monitor device.
FIG. 15 illustrates exemplary pie chart icons as human-readable identifiers on a proximal surface of a monitor device.

FIG. 14 illustrates exemplary character matrices 26AO-26AR as human-readable identifiers on a proximal surface of a monitor device 6. As illustrated, the character matrices 26AO-26AR may include a 2×2 matrix that includes any combination of Latin letters consisting of 26 characters (A-Z) and Arabic numerals consisting of ten different characters (0-9). However, in other embodiments, the character matrices 26AO-26AR may have more or fewer rows than 2 rows and/or more or fewer columns than 2 columns. Additionally, or alternatively, the character matrices 26AO-26AR may only include Latin letters or only include Arabic numerals.

In embodiments, the character matrices 26AO-26AR may be located on a proximal side of the monitor device 6. Additionally, or alternatively, the character matrices 26AO-26AR may be on a distal surface of the monitor device 6. While the character matrices 26AO-26AR are illustrated as being located to the right of the charging terminals 29, the character matrices 26AO-26AR may be located above the charging terminals 29, below the charging terminals 29, to the left of the charging terminals 29, and/or diagonally the charging terminals 29.

FIG. 15 illustrates exemplary pie chart icons 26AS-26AV as human-readable identifiers on a proximal surface of a monitor device 6. As illustrated, the pie chart icons 26AS-26AV may have different fill levels in order to distinguish between the monitor devices 6. For example, the pie chart icons 26AS-26AV may a quarter full as shown in the pie chart icon 26AS, half full as shown in the pie chart icon 26AT, three-quarters full as shown in the pie chart icon 26AU, completely full as shown in the pie chart icon 26AV, or any level in between.

In embodiments, the pie chart icons 26AS-26AV may be located on a proximal side of the monitor device 6. Additionally, or alternatively, the pie chart icons 26AS-26AV may be on a distal surface of the monitor device 6. While the pie chart icons 26AS-26AV are illustrated as being located to the right of the charging terminals 29, the pie chart icons 26AS-26AV may be located above the charging terminals 29, below the charging terminals 29, to the left of the charging terminals 29, and/or diagonally the charging terminals 29.

Figure 16:
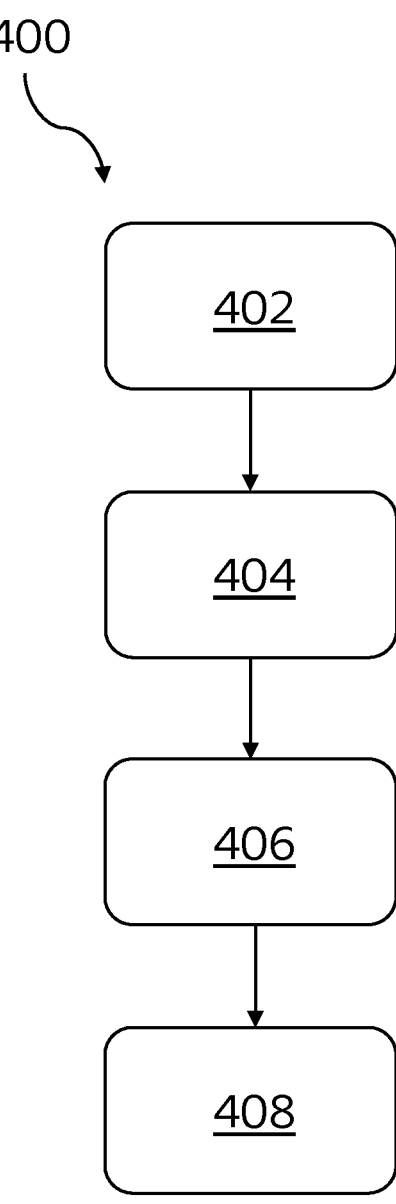
FIG. 16 illustrates an exemplary flow diagram of a method for manufacturing a plurality of monitor devices.

FIG. 16 illustrates an exemplary flow diagram of a method 400 for manufacturing a plurality of monitor devices. According to embodiments, the method comprises manufacturing a first monitor device (block 402) and manufacturing a second monitor device (block 404). The method 400 further comprises marking the first monitor device with a first human-readable identifier (block 406) and marking the second monitor device with a second human-readable identifier (block 408), wherein the first human readable identifier is different than the second human-readable identifier. In alternative embodiments, the marking of the first monitor device with a first human-readable identifier (block 406) is performed before manufacturing a second monitor device (block 404) and marking the second monitor device with a second human-readable identifier (block 408).

As stated above, manufacturing monitor devices having different human-readable identifiers allow a user of an ostomy system to have two monitoring devices that the user is able to reliable distinguish, for instance if one has a low battery level and the other is fully charged. In contrast, without the different human-readable identifiers, a user would not be able to distinguish between identical looking monitor devices. As such, a user may not be able to determine which monitor device has a low battery and which monitor device has a full battery. Therefore, the different human-readable identifiers facilitate the human-machine interaction by making it easy for the user to input to the ostomy system which devices are available, and by allowing the system to easily identify to the user the status of each device.

In embodiments, each of the first and second human-readable identifiers comprises maximally four characters providing at least 50,000 different combinations, such as to render the human-readable identifiers effectively different through the low possibility (<1:50,000) of selecting a second monitor device with a human-readable identifier identical to a first human-readable identifier. Additionally, or alternatively, the characters may be selected from Latin letters and/or Arabic numerals.

Additionally, or alternatively, each of the first and second human-readable identifiers may be selected from a combination of characters, a color, a geometric shape, a pie chart icon, and/or a flat design icon.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

The invention claimed is:

1. An ostomy system comprising:
an ostomy appliance comprising a sensor assembly;
at least two monitor devices, including a first monitor device having a first human-readable identifier and a second monitor device having a second human-readable identifier, each of the at least two monitor devices being configured to collect data from the sensor assembly; and
an accessory device comprising a set of instructions that, when executed by the accessory device, cause the accessory device to perform a set of operations, the set of operations comprising:
creating, in response to a first user input indicating the first-human readable identifier, a first monitor device profile associated with the first human-readable identifier; and
creating, in response to a second user input indicating the second human-readable identifier, a second monitor device profile associated with the second human-readable identifier.

2. The ostomy system according to claim 1, wherein the accessory device comprises a first interface configured to communicate with each of the at least two monitor devices and a user interface configured to receive at least one of the first user input or the second user input.

3. The ostomy system according to claim 2, wherein;
each of the first and second monitor device profiles is selectable by a user through the user interface,
the accessory device, in response to receiving the first user input indicative of the first monitor device profile being selected, is configured to transmit a first device signal to the first monitor device indicative of the first monitor device profile being selected, and
the accessory device, in response to receiving the second user input indicative of the second monitor device profile being selected, is configured to transmit a second device signal to the second monitor device indicative of the second monitor device profile being selected.

4. The ostomy system according to claim 2, wherein the user interface of the accessory device is configured to display an operating status of each of the at least two monitor devices.

5. The ostomy system according to claim 4, wherein the operating status is indicative of a battery level of a battery of each of the at least two monitor devices.

6. The ostomy system according to claim 4, wherein the operating status is indicative of a data collection mode of each of the at least two monitor devices.

7. The ostomy system according to claim 2, wherein the set of operations performed by the accessory device to further comprises:
obtaining first monitor data from the first monitor device; and
obtaining second monitor data from the second monitor device.

8. The ostomy system according to claim 7, wherein the set of operations performed by the accessory device to further comprises pooling the first monitor data and the second monitor data.

9. The ostomy system according to claim 1, wherein each of the first and second human-readable identifiers comprises a set of characters selected from Latin letters and Arabic numerals.

10. The ostomy system according to claim 1, wherein each of the first and second human-readable identifiers is selected from a combination of characters, a color, a geometric shape, a pie chart icon, and a flat design icon.

11. The ostomy system according to claim 1, wherein the first and second human-readable identifiers are provided by means of engraving, dyeing, or printing on the first and second monitor devices, respectively.

12. The ostomy system according to claim 2 further comprising a server configured to communicate with the accessory device.

13. The ostomy system according to claim 12, wherein the set of operations performed by accessory device further comprises:

obtaining first monitor data from the first monitor device;

obtaining second monitor data from the second monitor device; and providing the first monitor data and second monitor data from the accessory device to the server, thereby pooling the first monitor data and the second monitor data in a unique user profile at the server.

14. The ostomy system of claim 1, wherein the first human-readable identifier is different than the second human-readable identifier, thereby uniquely identifying each of the first monitor device and the second monitor device.

15. The ostomy system of claim 1, wherein each of the first and second human-readable identifiers comprises maximally four characters providing at least 50,000 different combinations.

\* \* \* \* \*